(12) United States Patent
Kroll

(10) Patent No.: US 10,252,069 B1
(45) Date of Patent: Apr. 9, 2019

(54) MICRO-CHARGE ICD LEAD TESTING METHOD AND APPARATUS

(71) Applicant: Lambda Nu Technology LLC, Crystal Bay, MN (US)

(72) Inventor: Mark W. Kroll, Crystal Bay, MN (US)

(73) Assignee: Lambda Nu Technology LLC, Orono, MN (US)

( * ) Notice: Subject to any disclaimer, the term of this patent is extended or adjusted under 35 U.S.C. 154(b) by 0 days.

(21) Appl. No.: 15/356,962

(22) Filed: Nov. 21, 2016

Related U.S. Application Data

(60) Provisional application No. 62/391,520, filed on May 2, 2016, provisional application No. 62/386,162, filed on Nov. 19, 2015.

(51) Int. Cl.
| | | |
|---|---|---|
| *A61N 1/00* | (2006.01) | |
| *A61N 1/39* | (2006.01) | |
| *A61N 1/05* | (2006.01) | |
| *A61N 1/08* | (2006.01) | |

(52) U.S. Cl.
CPC .......... *A61N 1/3925* (2013.01); *A61N 1/0563* (2013.01); *A61N 1/08* (2013.01); *A61N 1/3956* (2013.01); *A61N 2001/083* (2013.01)

(58) Field of Classification Search
CPC .......... A61N 2001/083; A61N 1/36142; A61N 1/37; A61N 1/3718; A61N 1/39; A61N 1/3925; A61N 1/39563; A61N 1/3975; A61N 1/39046; A61N 1/3912; A61N 1/3981
See application file for complete search history.

(56) References Cited

U.S. PATENT DOCUMENTS

| | | |
|---|---|---|
| 3,599,055 A | 8/1971 | Bloom |
| 4,766,549 A | 8/1988 | Schweitzer, III et al. |
| 5,003,975 A | 4/1991 | Hafelfinger et al. |
| 5,231,987 A | 8/1993 | Robson |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook A Guide to Measurement Technology and Techniques 4th Edition," Agilent Technologies, Inc., Jun. 17, 2009, 140 pages.

(Continued)

*Primary Examiner* — Scott M. Getzow
(74) *Attorney, Agent, or Firm* — Patterson Thuente Pedersen, P.A.

(57) ABSTRACT

Systems and methods for detecting lead anomalies by detecting overcurrent conditions caused by the delivery of high voltage test pulses configured to minimize patient sensation. Patient sensation is minimized by limiting the total charge delivered in either a positive or negative test pulse by limiting duration, and/or by cancelling nerve activations by delivery of an opposite phase cancellation pulse as part of a biphasic test pulse. Embodiments include high-speed H-bridge switches, and micro-coulomb test capacitors to control total charge and duration. Embodiments detect anomalies when an overcurrent circuit detects a current above a threshold passing through an electrode that is not directly energized.

22 Claims, 19 Drawing Sheets

(56) References Cited

U.S. PATENT DOCUMENTS

| | | | |
|---|---|---|---|
| 5,243,980 A | 9/1993 | Mehra | |
| 5,361,776 A | 11/1994 | Samuelson et al. | |
| 5,405,363 A | 4/1995 | Kroll et al. | |
| 5,453,698 A | 9/1995 | Williams et al. | |
| 5,557,210 A | 9/1996 | Cappa et al. | |
| 5,741,311 A | 4/1998 | McVenes et al. | |
| 5,755,742 A | 5/1998 | Schuelke et al. | |
| 5,897,577 A | 4/1999 | Cinbis et al. | |
| 5,944,746 A | 8/1999 | Kroll | |
| 6,104,954 A | 8/2000 | Blunsden | |
| 6,317,633 B1 | 11/2001 | Jorgenson et al. | |
| 6,415,179 B1 | 7/2002 | Pendekanti et al. | |
| 6,445,951 B1 | 9/2002 | Mouchawar | |
| 6,490,486 B1 | 12/2002 | Bradley | |
| 6,580,948 B2 | 6/2003 | Haupert et al. | |
| 6,928,325 B2 | 8/2005 | Zhu et al. | |
| 7,047,083 B2 | 5/2006 | Gunderson et al. | |
| 7,081,130 B2 | 7/2006 | Jang | |
| 7,120,563 B2 | 10/2006 | Bechhoefer et al. | |
| 7,289,851 B2 | 10/2007 | Gunderson et al. | |
| 7,369,893 B2 | 5/2008 | Gunderson | |
| 7,454,249 B1 | 11/2008 | Bornzin et al. | |
| 7,623,919 B2 | 11/2009 | Goetz et al. | |
| 7,747,320 B1 | 6/2010 | Kroll et al. | |
| 7,764,998 B1 | 7/2010 | Raddatz | |
| 8,200,330 B2 | 6/2012 | Kroll et al. | |
| 8,209,007 B2 * | 6/2012 | McIntyre | A61N 1/39 607/5 |
| 8,352,033 B2 | 1/2013 | Kroll | |
| 8,457,742 B2 | 6/2013 | Jacobson | |
| 8,463,382 B2 | 6/2013 | Jorgenson et al. | |
| 8,463,384 B2 | 6/2013 | Germanson et al. | |
| 8,467,872 B2 | 6/2013 | Hareland | |
| 8,498,706 B2 | 7/2013 | Pei et al. | |
| 8,577,457 B2 | 11/2013 | Miller et al. | |
| 8,644,932 B2 | 2/2014 | Seifert et al. | |
| 8,682,436 B2 | 3/2014 | Ghosh et al. | |
| 8,700,156 B2 | 4/2014 | Kroll | |
| 8,812,103 B2 | 8/2014 | Kroll et al. | |
| 8,825,158 B2 | 9/2014 | Swerdlow | |
| 9,272,150 B2 | 3/2016 | Kroll et al. | |
| 9,427,577 B2 | 8/2016 | Kroll et al. | |
| 9,486,624 B2 | 11/2016 | Swerdlow | |
| 9,675,799 B2 | 6/2017 | Kroll et al. | |
| 9,814,876 B2 | 11/2017 | Swerdlow | |
| 9,821,156 B2 | 11/2017 | Kroll et al. | |
| 9,827,416 B2 | 11/2017 | Swerdlow | |
| 2003/0004552 A1 | 1/2003 | Plombon et al. | |
| 2003/0036772 A1 | 2/2003 | Saphon et al. | |
| 2004/0010303 A1 | 1/2004 | Bolea et al. | |
| 2004/0068301 A1 | 4/2004 | Waltman et al. | |
| 2004/0158290 A1 | 8/2004 | Girouard et al. | |
| 2004/0230385 A1 | 11/2004 | Bechhoefer et al. | |
| 2005/0137636 A1 | 6/2005 | Gunderson et al. | |
| 2005/0187586 A1 | 8/2005 | David et al. | |
| 2005/0256547 A1 | 11/2005 | Stahmann et al. | |
| 2006/0025828 A1 | 2/2006 | Armstrong et al. | |
| 2006/0116747 A1 | 6/2006 | Eick et al. | |
| 2006/0135886 A1 | 6/2006 | Lippert et al. | |
| 2006/0241513 A1 | 10/2006 | Hatlestad | |
| 2006/0265038 A1 | 11/2006 | Hagen et al. | |
| 2007/0208387 A1 | 9/2007 | Mower | |
| 2008/0208271 A1 | 8/2008 | Sih et al. | |
| 2008/0309351 A1 | 12/2008 | Stewart et al. | |
| 2009/0099615 A1 | 4/2009 | Kroll | |
| 2009/0270938 A1 | 10/2009 | Pei et al. | |
| 2009/0292331 A1 | 11/2009 | Gunderson et al. | |
| 2009/0299431 A1 | 12/2009 | Schecter | |
| 2009/0299432 A1 | 12/2009 | Stadler et al. | |
| 2009/0306735 A1 | 12/2009 | Lagercrantz et al. | |
| 2010/0179446 A1 | 7/2010 | Bojovic et al. | |
| 2010/0179538 A1 | 7/2010 | Podhajsky | |
| 2010/0204758 A1 | 8/2010 | Boon et al. | |
| 2010/0228307 A1 | 9/2010 | Kroll et al. | |
| 2010/0324629 A1 | 12/2010 | Jorgenson et al. | |
| 2011/0054554 A1 | 3/2011 | Swerdlow | |
| 2011/0054556 A1 | 3/2011 | Swerdlow | |
| 2011/0054558 A1 | 3/2011 | Gunderson et al. | |
| 2011/0160808 A1 | 6/2011 | Lyden et al. | |
| 2011/0160829 A1 | 6/2011 | Foster et al. | |
| 2011/0230741 A1 | 9/2011 | Liang et al. | |
| 2011/0245888 A1 * | 10/2011 | Badelt | A61N 1/3931 607/6 |
| 2012/0035491 A1 | 2/2012 | Mahajan et al. | |
| 2012/0191153 A1 | 7/2012 | Swerdlow et al. | |
| 2012/0197331 A1 | 8/2012 | Germanson et al. | |
| 2012/0197365 A1 | 8/2012 | Germanson et al. | |
| 2013/0013038 A1 | 1/2013 | Miller | |
| 2013/0030496 A1 | 1/2013 | Karamanoglu et al. | |
| 2013/0123871 A1 | 5/2013 | Kroll | |
| 2013/0165986 A1 | 6/2013 | Ghosh et al. | |
| 2013/0304139 A1 | 11/2013 | Musley et al. | |
| 2013/0304160 A1 | 11/2013 | Gunderson et al. | |
| 2013/0325079 A1 | 12/2013 | Kroll et al. | |
| 2013/0325080 A1 * | 12/2013 | Kroll | A61N 1/3925 607/6 |
| 2014/0155947 A1 | 6/2014 | Kroll et al. | |
| 2014/0324123 A1 | 10/2014 | Kroll et al. | |
| 2014/0371831 A1 | 12/2014 | Swerdlow | |
| 2015/0005862 A1 | 1/2015 | Kroll et al. | |
| 2015/0088213 A1 | 3/2015 | Swerdlow | |
| 2015/0151118 A1 | 6/2015 | Kroll et al. | |
| 2015/0273225 A1 | 10/2015 | Swerdlow et al. | |
| 2016/0250462 A1 | 9/2016 | Kroll et al. | |
| 2016/0271390 A1 | 9/2016 | Kroll et al. | |
| 2016/0375239 A1 | 12/2016 | Swerdlow | |
| 2017/0120045 A1 | 5/2017 | Swerdlow | |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Characterization of Different Subsets of Atrial Fibrillation in General Practice in France: The ALFA Study," The College of French Cardiologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

(56) References Cited

OTHER PUBLICATIONS

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc. Electrophysiol., 2001, pp. 592-599.

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by High-Frequency Biphasic Electrical Currents," IEEE T-BME, 2005, p. 1323.

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.

Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.

Iwasawa J, et al., "Discrimination algorithm of an implantable cardioverter defibrillator in a case with a lead dislodgement," Heart Rhythm, vol. 11, 2014, pp. S491-S492.

Ruiz-Salas A, et al., "Inappropriate shock due to late dislocation of electrode," International Journal of Cardiology, vol. 199, 2015, pp. 229-231.

Veltmann C, et al., "Fatal inappropriate ICD shock," J. Cardiovasc. Electrophysiol, vol. 18(3), 2007, pp. 326-328.

Application and File history for U.S. Appl. No. 12/868,056, filed Aug. 25, 2010, now U.S. Pat. No. 8,825,158. Inventor Swerdlow.

Application and File history for U.S. Appl. No. 13/735,599, filed Jan. 7, 2013, now U.S. Pat. No. 8,700,156. Inventor Kroll.

Application and File history for U.S. Appl. No. 13/842,838, filed Mar. 15, 2013. Inventor Kroll.

Application and File history for U.S. Appl. No. 12/252,310, filed Oct. 15, 2008, now U.S. Pat. No. 8,352,033. Inventor: Kroll.

Application and File history for U.S. Appl. No. 13/843,145, filed Mar. 15, 2013, now U.S. Pat. No. 8,812,103. Inventors: Kroll et al.

Application and File history for U.S. Appl. No. 13/833,477, filed Mar. 15, 2013. Inventors: Kroll et al.

Application and File history for U.S. Appl. No. 14/224,876, filed Mar. 25, 2014. Inventors: Kroll et al.

Application and File history for U.S. Appl. No. 14/224,281, filed Mar. 25, 2014. Inventors: Kroll et al.

Application and File history for U.S. Appl. No. 14/203,688, filed Mar. 11, 2014. Inventors: Kroll et al.

Application and File history for U.S. Appl. No. 14/224,335, filed Mar. 25, 2014. Inventors: Kroll et al.

Application and File history for U.S. Appl. No. 14/453,679, filed Aug. 7, 2014. Inventors: Kroll et al.

Application and File history for U.S. Appl. No. 14/472,027, filed Aug. 28, 2014. Inventors: Kroll et al.

Application and File history for U.S. Appl. No. 15/054,538, filed Feb. 26, 2016. Inventors: Kroll et al.

Application and File history for U.S. Appl. No. 15/080,343, filed Mar. 24, 2016. Inventors: Kroll et al.

Application and File history for U.S. Appl. No. 15/344,864, filed Nov. 7, 2016. Inventors: Swerdlow.

Application and File history for U.S. Appl. No. 15/013,201, filed Feb. 4, 2016. Inventors: Swerdlow.

Application and File history for U.S. Appl. No. 15/810,324, filed Nov. 13, 2017. Inventors: Swerdlow.

* cited by examiner

MICRO-CHARGE ICD LEAD TESTING METHOD AND APPARATUS

CROSS-REFERENCE TO RELATED APPLICATIONS

This application claims priority to U.S. Provisional Patent App. No. 62/386,162 filed Nov. 19, 2015, and U.S. Provisional Patent App. No. 62/391,520 filed May 2, 2016, the disclosures of which are incorporated by reference herein.

TECHNICAL FIELD

The present invention relates generally to electrical therapeutic systems for applying electrical therapy to patients for detecting and treating cardiac arrhythmias. More particularly, the invention relates to a method and apparatus for analyzing implantable cardiac leads to promote patient safety by evaluating possible issues with implantable cardiac lead integrity, including partial insulation failures, especially in multilumen leads.

BACKGROUND

Implantable cardioverter defibrillators (ICDs) are used to provide various types of therapy to treat cardiac arrhythmias in a patient, including, for example defibrillation. These devices typically consist of a hermetic housing implanted into a patient and connected to at least one defibrillation electrode. The housing of the ICD contains electronic circuitry for monitoring the condition of the patient's heart, usually through sensing electrodes, and also contains the battery, high voltage circuitry and control circuitry to generate, control and deliver defibrillation shocks. Typically, one or more of the defibrillation electrodes are connected to circuitry within the ICD via one or more implantable cardiac leads that extend from the housing to the defibrillation electrodes. The housing of the ICD (usually referred to as the "CAN") may also include one or more defibrillation electrodes configured on the exterior of the housing.

Implantable transvenous ICD leads are generally elongated lead bodies made of biocompatible insulation material(s) including multiple parallel lumens with each lumen carrying one or more conductors that run between connectors on a proximal end to electrodes proximate a distal portion of the implantable cardiac lead. The number of conductors required for true-bipolar ICD implantable cardiac leads is typically four (two conductors for sensing and pacing that provide conduction paths for a lower power sensed signal and a ground return, and two conductors for therapy that provide conduction paths for higher power defibrillation shocks). Integrated-bipolar leads can combine 1 defibrillation electrode as a pace-sense electrode and thus have only three conductors. In addition, a separate center inner coil and stylet lumen may be provided for use in implanting the ICD implantable cardiac lead. The center inner coils may also include conductors that carry electric signals to pacing sense/therapy electrodes. The diameter of the implantable cardiac lead body must be small enough to navigate the blood vessels through which the implantable cardiac lead is implanted, while still being robust enough to maintain electrical and mechanical integrity over the course of bending and movement during hundreds or thousands of heart beats and respirations.

The long-term reliability and safety of implantable cardiac leads is a significant issue. Conductor anomalies in the implantable cardiac leads for ICDs can result in morbidity or mortality from loss of pacing, inappropriate ICD shocks, or ineffective treatment of ventricular tachycardia or ventricular fibrillation. The early diagnosis of conductor anomalies for implantable cardiac leads is a critically important step in reducing these issues and making ICDs safer.

A particular conductor anomaly that is unique to implantable cardiac leads occurs when a conductor migrates through the soft silicone material of the implantable cardiac lead body away from the original position of the conductor within a lumen. In some cases, the cable including the conductor may abrade against the lumen that constrains it to migrate outwardly within the silicone implantable cardiac lead body ("inside-out" abrasion) without breaking through the external insulating layer of the implantable cardiac lead body. In other cases, the conductor may continue to abrade against the silicone elastomer lead body until it breaks through the surface and become externalized and exposed to body fluids and tissue. At this stage, it may be detected by fluoroscopy. Initially, the thin polymer (ETFE) insulating layer surrounding the cable remains intact, at least without delivery of high-voltage shocks. Over time, this ETFE secondary insulating layer can become abraded or damaged due one of various mechanisms. Exposed conductors can also result in sensing of nonphysiological electrical signals, "noise", if the exposed conductor is connected to a sensing electrode. This results in incorrect detection of ventricular tachycardia or fibrillation (over-sensing) that may result in unnecessary painful shocks. Even more worrisome, this problem may result in failed defibrillation shocks if the conductor is connected to the primary (distal) shock coil located in the right ventricle (RV). In this case, the patient will likely die of the arrhythmia unless promptly defibrillated by an external defibrillator. Failed defibrillation shocks are particularly likely if the conductor to the RV shock coil abrades against the proximal shock coil in the superior vena cava (SVC) resulting in a short circuit when a shock is needed. Such "under-the-coil" abrasions may occur without exteriorized cables so that they are undetectable by fluoroscopy, hence only detected when a shock is delivered. It is not known how often or the extent to which early-stage failures of outer insulation may compromise sensing and/or defibrillation.

Some leads have an additional, abrasion-resistant coating of silicone-polyurethane copolymer (e.g. Optim™) tubing on the external surface. Intact, external tubing prevents cables that have abraded through their lumens from exteriorizing, but it does not alter the fundamental process of "inside-out" abrasion. Under the shock-coils, coated leads are identical to similarly-designed leads without tubing, and they provide no additional protection against inside-out, cable-coil abrasion. It is desirable to detect inside-out abrasions in coated leads even when an electrical abnormality resulting in lead failure does not occur.

Numerous approaches have been suggested for trying to diagnosis and correct for the problems of implantable cardiac lead failures and anomalies. Most involve the classic approach of subjecting the implantable cardiac lead to a periodic test pulse, measuring the direct-current impedance of the test pulse and then comparing that impedance to an expected range of acceptable impedance values. In implantable cardiac leads, however, only one end of the conductor is generally accessible for testing purposes and changes in system impedance may be dominated by changes unrelated to conductor or implantable cardiac lead faults. For example, the reference impedance for pace-sense conductors (the metal only) is in the range of about 15-50Ω, and usually is constant within about 10% for an individual conductor. But the reference impedance for the combined electrode-tissue interface and connected body tissue ranges from about 300Ω to greater than 1000Ω. More importantly, biological variations of up to 300Ω are common, and variations of greater than 1000Ω may occur without conductor or insulation failures.

U.S. Pat. Nos. 8,700,156, and 8,352,033 (the disclosures of which are incorporated by reference herein) to Kroll teach an ICD circuit for discharging a small capacitor for lead testing. However, that approach has a significant implementation complication that renders it unattractive as it requires the addition of high-energy switches to isolate the main high-energy therapeutic capacitors during testing.

A very critical problem presents when the insulation is sufficient to withstand low-voltage test pulses and is thus deemed to be intact. If the patient needs high-voltage therapy then a defibrillation shock of typically 800 or 900 V is delivered. This high-voltage shock can arc through the thin insulation and result in a catastrophic failure.

A need therefore exists for methods and apparatus that can analyze and identify implantable cardiac lead conductor anomalies at the subclinical stage, before they present as a clinical problem, and do so with a high sensitivity and specificity that minimizes false positives for implantable cardiac lead conductor anomalies.

SUMMARY

Embodiments of the present disclosure include systems and methods for detecting lead anomalies by detecting overcurrent conditions caused by the delivery of high voltage test pulses configured to minimize patient sensation. Patient sensation is minimized by limiting the total charge delivered in either a positive or negative test pulse by limiting duration, and/or by cancelling nerve activations by delivery of an opposite phase cancellation pulse as part of a biphasic test pulse.

In an embodiment, an implantable cardioverter defibrillator is electrically connected to at least two defibrillation electrodes, with at least one of the defibrillation electrodes located remotely from the defibrillator along a lead. The defibrillator includes at least one high voltage transformer electrically connected between a battery and at least one high voltage capacitor, with positive and negative terminals. The defibrillation circuit also includes an H-bridge with at least two circuit paths, connected in parallel to the at least one high voltage capacitor. Each path of the H-bridge includes a first switch connected in series to the negative terminal of the circuit path and to a defibrillation electrode and a second switch connected in series to the defibrillation electrode and the positive terminal of the circuit path. Each of the defibrillation electrodes is isolated from the other defibrillation electrodes by at least patient tissue or lead insulation. The defibrillation circuit also includes an overcurrent circuit, electrically connected in series between the H-bridge and the one high voltage capacitor, and configured to detect current above a threshold. A controller is configured to charge the at least one high voltage capacitors, deliver a short duration, high-voltage, biphasic test pulse between at least two of the defibrillation electrodes, and produce a signal indicative of an anomaly in the lead when the overcurrent circuit detects a current above the threshold.

In embodiments, the defibrillation electrodes be combinations of a can electrode, a superior vena cava coil electrode, and a right ventricular coil electrode.

In embodiments, a positive phase of the biphasic test pulse is delivered by closing the second switch on a first circuit path and the first switch on a second circuit path and the negative phase is delivered by opening the second switch on the first circuit path and the first switch on the second circuit path, and closing the first switch on the first circuit path and the second switch on the second circuit path. In embodiments, the total duration of the biphasic test pulse is one microsecond or less.

In embodiments, the implantable cardioverter defibrillator includes a test capacitor connected in parallel with at least the first or second switch of a circuit path including a defibrillation electrode on the lead (such as the RV coil electrode or the SVC coil electrode). In embodiments, the test capacitor has a capacitance between about 10 nF and 33.7 nF.

In embodiments, biphasic test pulse is delivered by delivering a positive phase by closing the second switch a circuit path not including the test capacitor for a first duration (which can be between about 0.3 and 2 microseconds, waiting for a cool down interval of a second duration (which can be about 5 microseconds), and delivering a negative phase by closing the first switch on the circuit path not including the test capacitor. In embodiments, the first and second switches of the circuit path not including the test capacitor are silicon controlled rectifiers configured to open when current flow ceases.

In embodiments, each phase of the biphasic test pulse has a duration of less than about 300 nanoseconds. In embodiments, the voltage of the biphasic test pulse is between about 400V and about 700V. In embodiments, the test pulses can be delivered at plurality of increasing voltages.

In embodiments an anomaly in an RV conductor of a lead is detected by delivering short duration, high-voltage, positive or negative test pulse between the RV coil electrode and the can electrode and detecting a short between the can electrode and RV coil electrode if the overcurrent circuit detects current above the threshold. In embodiments, the duration and voltage are chosen in order to deliver a total charge below about 4.25 μC, so no opposite phase cancellation pulse is required. In embodiments the duration is less than about 300 nanoseconds and the voltage is less than about 800V.

The present invention allows for high-voltage lead testing without the addition of any high-energy switches. In addition, embodiments allow for this testing without the addition of any switches at all to common defibrillation circuits.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
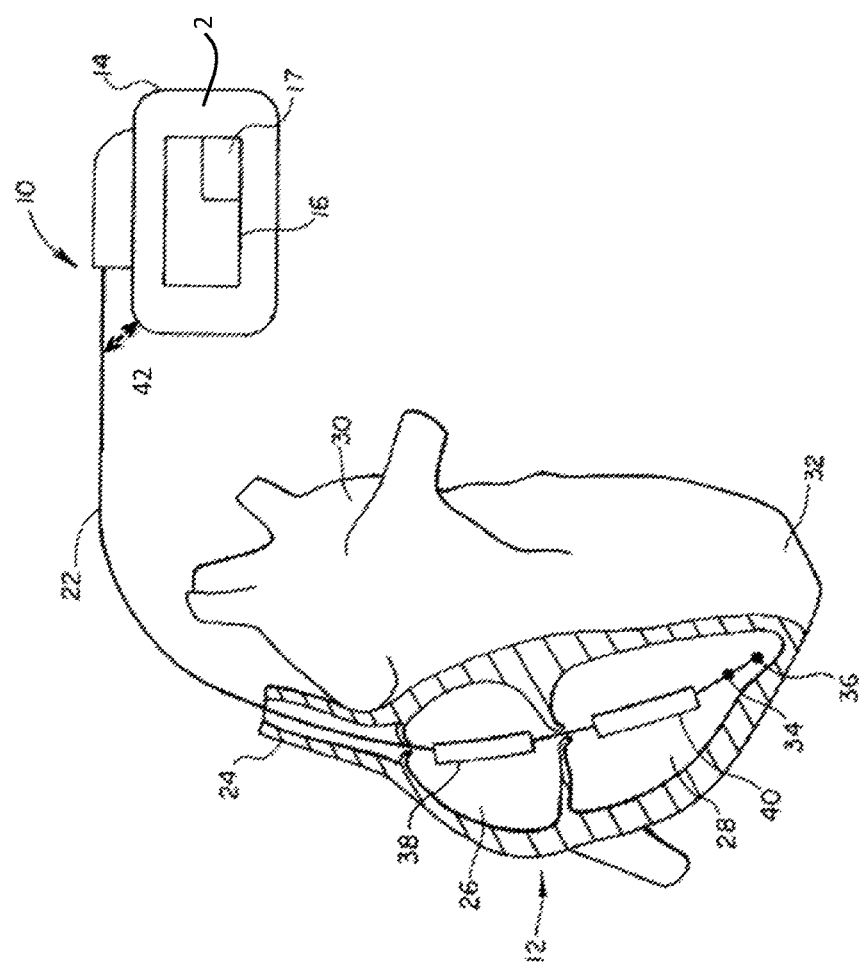
FIG. 1 is a schematic depicting an ICD connected to the heart of a patient by a lead that exhibits an insulation failure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1 depicts an implantable cardioverter defibrillator (ICD) 2 connected to a lead 10, which is implanted into the heart 12 of a patient. ICD 2 can include a controller, implemented in hardware, software, or firmware. ICD 2 is defined by a housing, on which is configured a can electrode (or simply can 14). Lead 10 can include one or more conductors, including right ventricular (RV) conductor 22 which can couple ICD 2 to RV coil 40 and, in dual-coil arrangements, superior vena cava conductor 23 which can couple ICD 2 to SVC coil 38. Lead 10 can further include insulation 24 surrounding one or more of the conductors. In order to simulate an insulation failure, insulation 24 has been abraded so that a short circuit 42 has been formed between can 14 and right RV conductor 22 or SVC conductor 23. In embodiments, ICD 2 may be connected to additional leads 10, in which case SVC conductor 23 and SVC coil 38 can reside on a separate lead to RV conductor 22 and RV coil 40. In embodiments, more or fewer leads, conductors and coils may be present. In addition, coils may be implanted in alternative locations, for example: the right atrium or left ventricle of heart 12, adjacent to the vagus or other nerve(s), or in contact with the brain of a patient.

Figure 2:
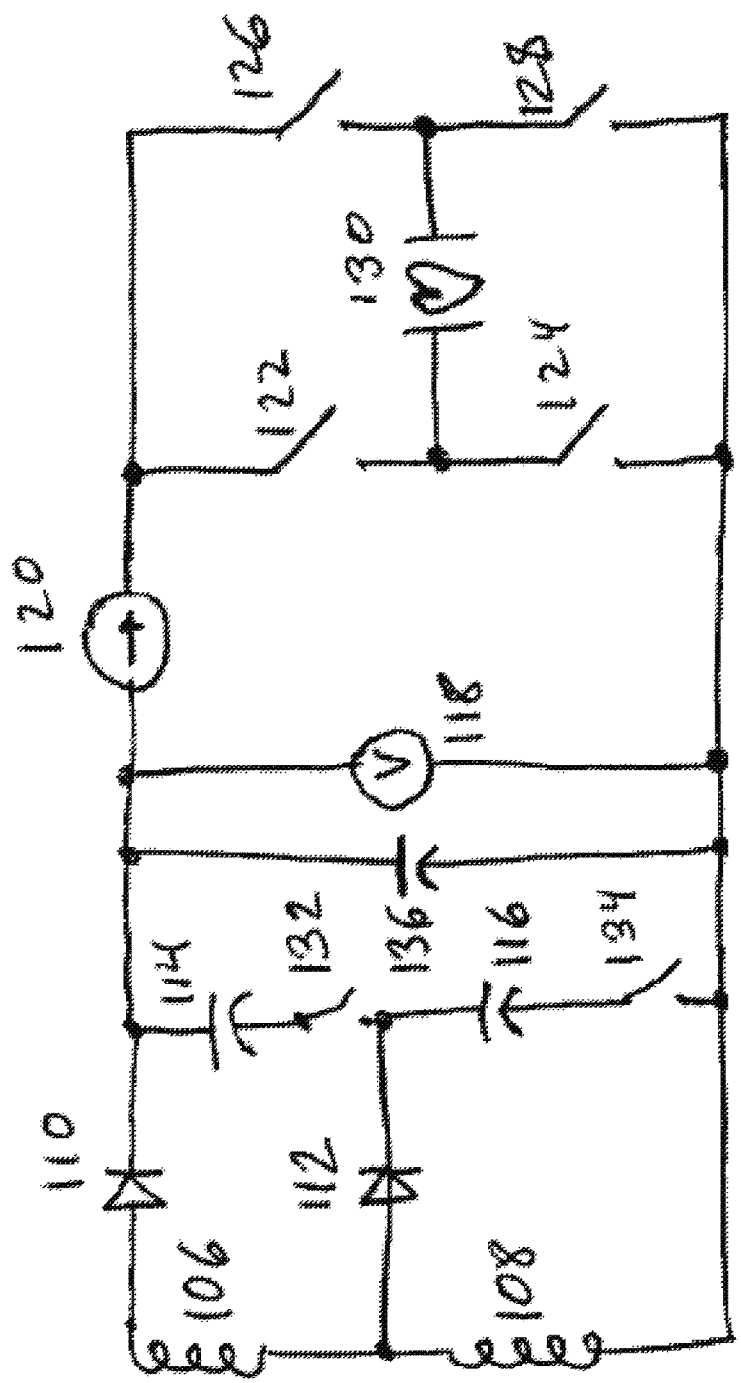
FIG. 2 is a diagram depicting a circuit capable of implementing embodiments of known high voltage insulation tests.

FIG. 2 is a diagram depicting a circuit capable of implementing embodiments of a prior art high voltage insulation test approach. One of the limitations of this prior art method is the requirement for additional high-voltage high current switches 132 and 134. This approach is also limited in that the H-bridge switches 122, 124, 126, and 128 are generally not capable of being turned off within microseconds and thus this approach could lead to painful shocks due to the large charges delivered.

Figure 3:
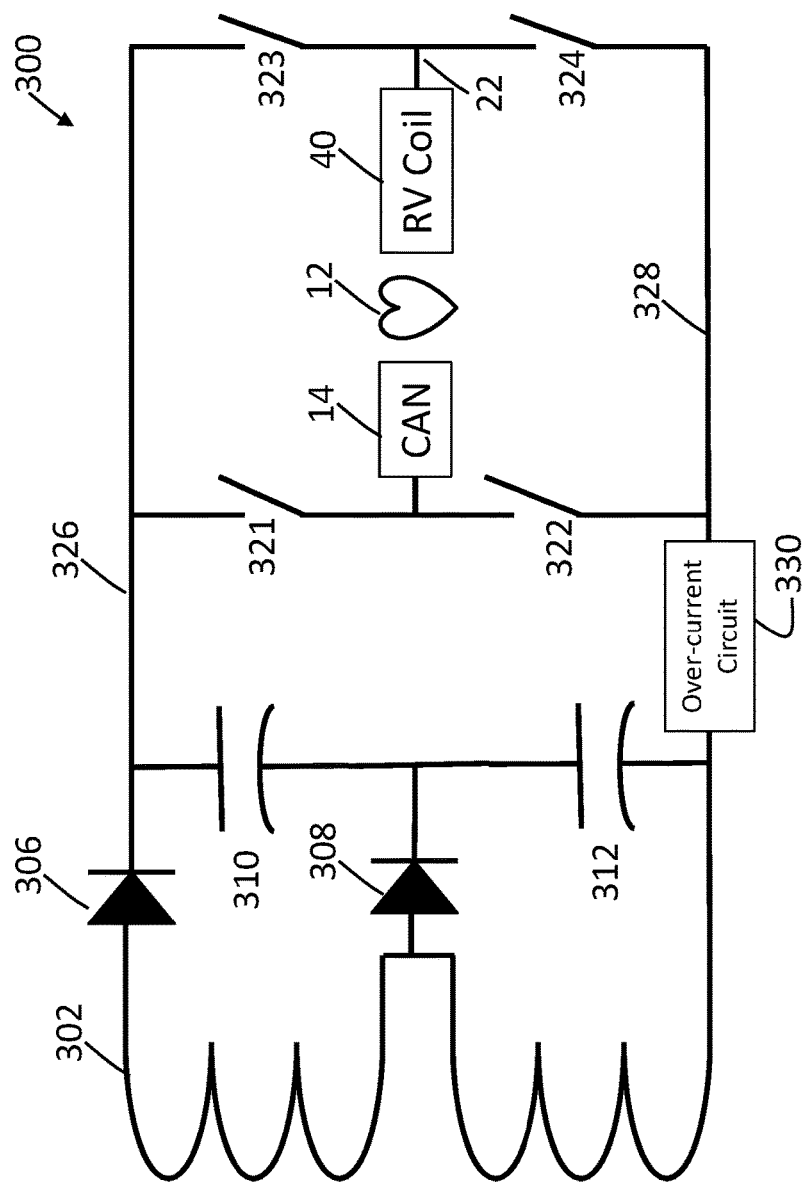
FIG. 3 is a diagram depicting a basic output circuit for an ICD, according to an embodiment.

FIG. 3 is a diagram depicting a simplified basic output circuit 300 for an ICD 2. Those of ordinary skill in the art will appreciate that circuit 300 is depicted in simplified form, and more components and connections may be provided. For example, the various components of circuit 300 can be electrically connected to ICD controller however these connections are not shown in FIG. 3. Transformer 302 is configured to deliver current through diodes 306 and 308 to charge therapeutic capacitors 310 and 312 which are arranged in series. An H-bridge 320 is formed by switches 321, 322, 323, and 324. ICD controller can open and close switches 321, 322, 323, and 324 as required. Can 14 of the ICD is coupled to switches 321 and 322. Upper rail 326 of H-bridge 320 couples therapeutic capacitors 310 and 312 to switches 321 and 324. Lower rail 328 of H-bridge 320 couples therapeutic capacitors 310 and 312 to switches 322 and 324. RV coil 40 is coupled to switches 323 and 324 via RV conductor 22. ICD controller can enable current to flow from RV coil 40 to CAN 14 via chest and heart 12 by manipulation of switches 321, 322, 323, and 324.

Overcurrent circuit 330 is connected to lower rail 328 of H-bridge 320 to quickly sense shorts and to remove current from the H-bridge 320 in order to prevent damage in case of a short among the leads or electronics of the H-bridge 320. Overcurrent circuit 330 can also be configured to send a signal back to control electronics in case such a short is detected. In typical applications, overcurrent circuit 330 is often be configured to shut off upon receipt of current of about 40 A. In embodiments, overcurrent circuit 330 can also be configured to shut off with upon receipt of current of about 10 A to inhibit unnecessary damage to the conductors and insulation during insulation tests. In embodiments, overcurrent circuit 330 can be software configurable, enabling the ICD controller to set the shutoff current at a higher value for normal operation and lower value for insulation testing. For simplicity overcurrent circuit 330 will not be repeated in the following drawings.

Those of ordinary skill in the art will appreciate that where lead 10 includes SVC conductor 23 and SVC coil 38, output circuit 300 will also include switches 325 and 326 (not shown) similar to those delivering current to and from CAN 14.

The embodiments described herein, for detecting an insulation failure in lead 10 causing a short circuit between RV conductor 22 and CAN 14, can also be performed between RV conductor 22 and SVC coil 38, or its conductor 23. These can be performed simultaneously (by "grounding" both the SVC coil 38 and CAN 14 to lower rail 328 of H-bridge 320) or sequentially by delivering separate voltage pulses to them. Therefore, those of ordinary skill in the art will appreciate that test pulses delivered via CAN 14 and RV coil 40 with respect to the circuits and methods described below, can also be delivered via SVC coil 38 and RV coil 40, or SVC coil 38 and CAN 14 as required.

Figure 4:
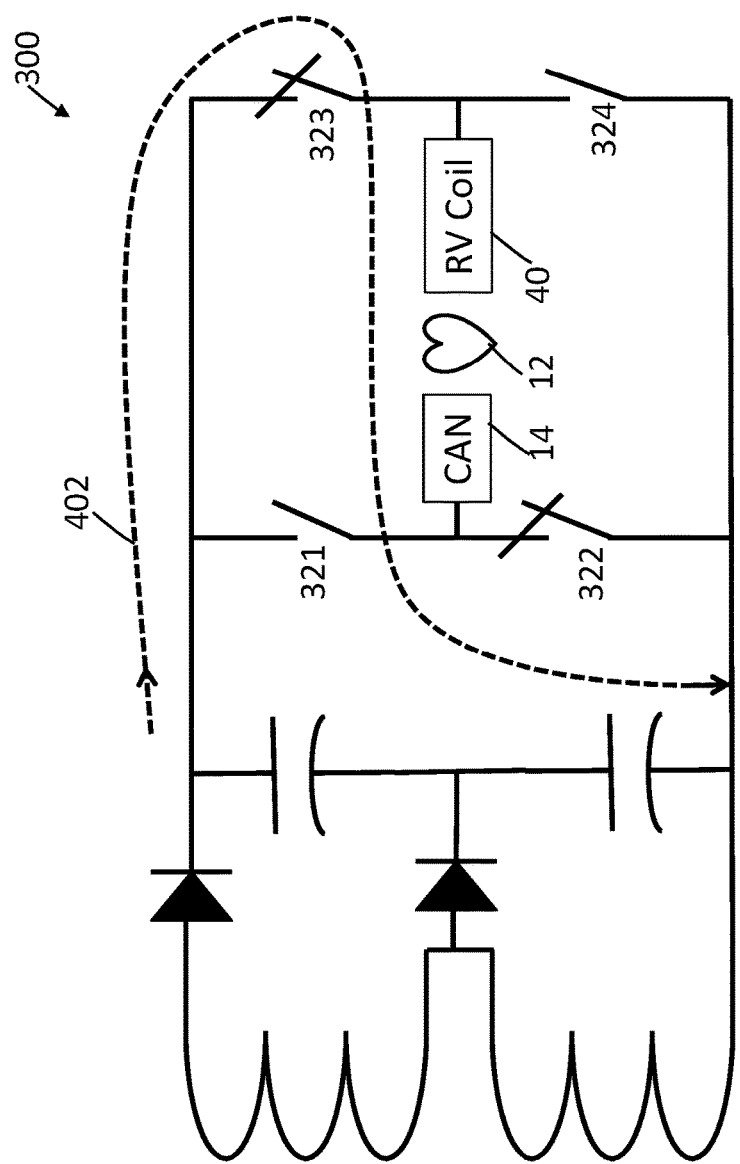
FIG. 4 is a diagram depicting the circuit of FIG. 3 as the ICD H-bridge delivers the positive phase of a biphasic shock, according to an embodiment.

FIG. 4 is a diagram depicting current flow (arrow 402) through circuit 300 during the delivery of the positive phase of a biphasic shock. Therapeutic capacitors 310 and 312 are charged up to the desired energy level. Then switches 322 and 323 are closed (turned "ON"). This switch closure enables current 402 (driven by positive voltage from therapeutic capacitors 310 and 312) to flow through RV coil to CAN 14 via the chest and heart 12. Current 402 then flows via switch 322 back to therapeutic capacitors 310 and 312.

Figure 5:
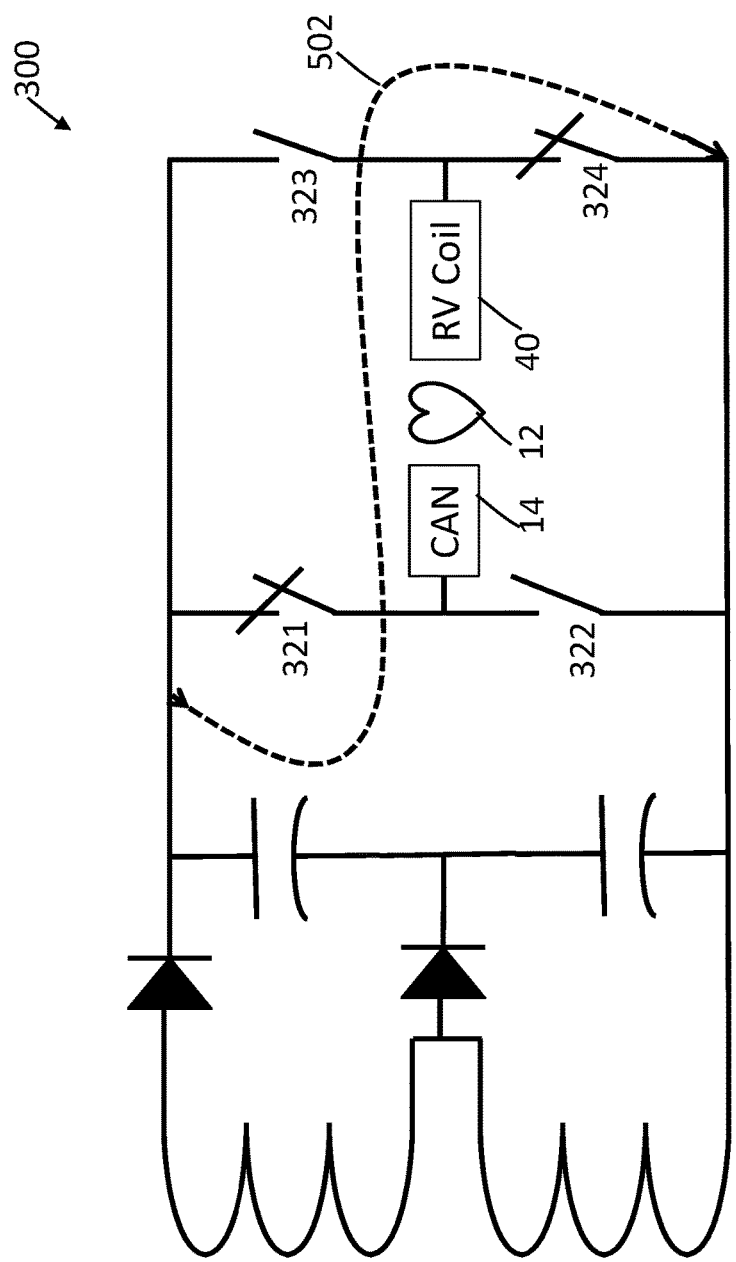
FIG. 5 is a diagram depicting the circuit of FIG. 3 as the ICD H-bridge delivers the negative phase of a biphasic shock, according to an embodiment.

FIG. 5 is a diagram depicting current flow (arrow 502) through circuit 300 during the delivery of the negative phase of a biphasic shock. The therapeutic capacitors are now charged at a reduced energy level because of the substantial charge delivered during the positive phase. Then switches 321 and 324 are closed (turned "ON"). This switch closure enables current 502 (driven by positive voltage from therapeutic capacitors 310 and 312) to flow through CAN 14 to RV coil 40 via chest and heart 12. Current 402 then flows via switch 324 back to therapeutic capacitors 310 and 312.

Therapeutic shock pulses delivered via circuit 300 can cause the patient to sense pain at intolerable levels due to the activation of nerve potentials, in particular in the sensitive A-delta subcutaneous nociceptors proximate can 14. This can be avoided by limiting the total charge delivered to the patient.

Figure 6:
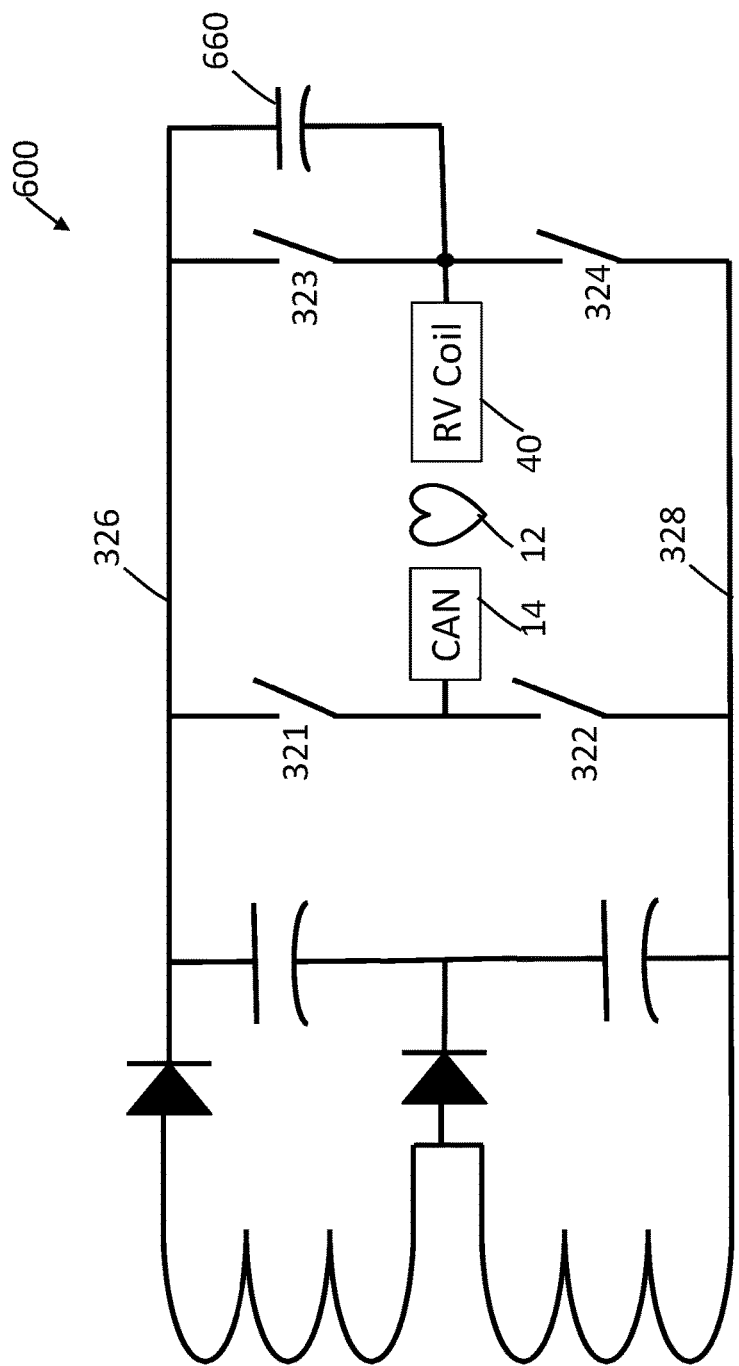
FIG. 6 is a diagram depicting an output circuit including a small capacitor, according to an embodiment.

FIG. 6 is a diagram depicting a modified output ICD output circuit 600, configured to deliver test pulses for lead integrity testing according to an embodiment. Circuit 600 is configured to deliver biphasic test pulses with phase durations of 1 microsecond or less. These test pulses are much shorter than therapeutic shocks which can have phase durations of a few milliseconds. In addition, circuit 600 is configured to deliver a total amount of charge that is unlikely to cause intolerable pain.

Circuit 600 can be essentially equivalent to circuit 300, with the addition of a test capacitor 660 across switch 323. Test capacitor 660 must withstand the full voltage of therapy capacitors 310 and 312, while delivering a test pulse with charge sufficiently strong to arc over insulation defects, resulting in activation of overcurrent circuit 330 but not strong enough to cause intolerable pain.

Those of ordinary skill in the art will appreciate that the intensity of a threshold stimulus is related to its duration, in that as the duration of the stimulus increases, the current necessary to activate nerve potentials decreases. Therefore, given data regarding patient tolerance of long duration pulses of known charge strength Q, it can be assumed that the patient tolerance will be similar for a test pulse at a charge strength that is equivalent to the intercept charge $Q_0$ (the minimum charge at which the equivalent number of nerve potentials would be activated, assuming infinite duration).

Figure 7:
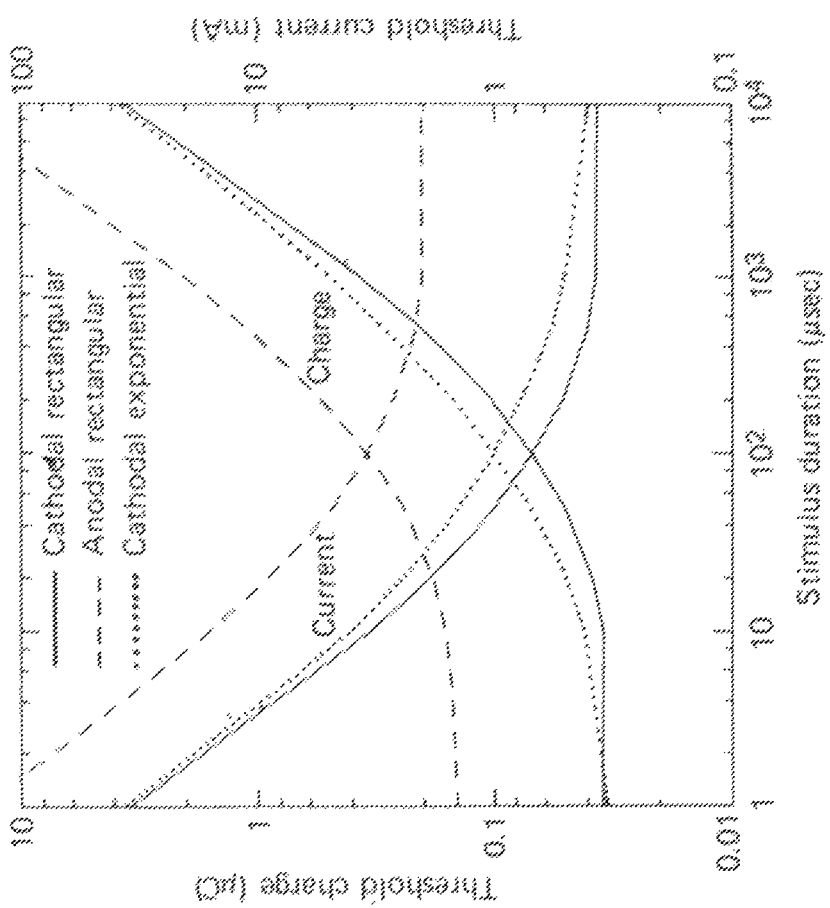
FIG. 7 is a chart depicting strength-duration curves for various monophasic pulses.

FIG. 7 is a chart depicting strength-duration curves for various monophasic pulses. In pacing textbooks, the strength-duration relationship is typically shown with the Lapicque equation:

$$I=I_r(1+d_c/d) \quad (1)$$

where $I_r$ is the "rheobase" current, or the minimal current amplitude that results in the polarization threshold being met assuming infinite duration, $d_c$ is the "chronaxie" duration, or the minimum amount of time needed to stimulate a muscle or nerve fiber, using an electric current that is twice the rheobase current, and d is the pulse duration.

The Lapicque equation is related to the Weiss equation which gives the relationship in terms of charge. Since Weiss is a linear equation it can be more robust for statistical calculations compared to the hyperbolic Lapicque formula. The Weiss equation can be derived from the Lapicque equation by multiplying through by the tested duration (d):

$$Q=Id=I_r d+I_r d_c \quad (2)$$

This can be simplified to more closely match Weiss' formulation:

$$Q=I_r d+Q_0 \quad (3)$$

Therefore, from equations 2 and 3 we can derive:

$$I_r = \frac{Q}{d + d_c} \quad (4)$$

and:

$$Q_0 = \frac{Q d_c}{d + d_c} \quad (5)$$

Table 1 below provides data regarding human patient tolerance of three longer duration pulses of strength Q are detailed in table 1 below. The intercept charge, $Q_0$, assuming a cutaneous perception chronaxie duration ($d_c$) of 270 µs, is calculated for each pulse. We can therefore estimate the pain thresholds for a "hot can" system in terms of the charge for a very narrow test pulse.

TABLE 1

| Source | Voltage V | Impedance Ω | Current (I) mA | Pulse Duration (d) ms | Charge (Q) µC | Patient Sensation | Intercept Charge ($Q_0$) µC | Implied C for 900 V (nF) |
|---|---|---|---|---|---|---|---|---|
| Unipolar Pacing | 10 | 500 | 20 | 1 | 20 | Tolerated | 4.25 | 4.7 |
| Unipolar 0.1 J shock | | | | 10 | 5000.0 | Not Tolerated | 131 | 146.1 |
| HVLI test (SJM) | 12 | 106.8 | 112.3 | 1000 | 112331.8 | Partially Tolerated | 30 | 33.7 |

As can be seen from Table 1, unipolar pacing is well-tolerated with 10 V pulses of 1 ms duration. This gives an intercept charge $Q_0$ of 4.25 µC so we can be confident that that this is a tolerable level of charge to be delivered between the RV coil 40 and can 14.

A unipolar test shock of 0.1 J is objectionable to patients and this is equivalent to an intercept charge $Q_0$ of 131 µC. This would be considered an intolerable level of charge and must be avoided.

Finally, a high voltage leading impedance (HVLI) test conducted by some St. Jude Medical ICDs delivers 12 V between RV coil 40 and can 14. This was found to be objectionable to some patients but in general fairly tolerable. Assuming that the impedance is about 106.8 (calculated based on Brewer J. E., Tvedt M. A., Adams T. P., Kroll M. W. *Low Voltage Shocks Have a Significantly Higher Tilt of the Internal Electric Field Than Do High Voltage Shocks*, 18 Pacing Clin. Electrophysiol. 1 214-220 (1995)), this pulse is equivalent to a intercept charge $Q_0$ of 30 µC and which can be considered a maximum charge.

Therefore, in order to reduce patient discomfort, test pulses for lead integrity testing should deliver between about 4.25 µC to about 30 µC.

The appropriate maximum capacitance of test capacitor 660 can therefore be determined based on the desired pulse charge strength assuming a typical maximum voltage in an ICD of 900 V. Based on the intercept charges, $Q_0$, of Table 1 we can calculate the required capacitance to deliver such a charge from:

$$C = \frac{Q_0}{V} \quad (6)$$

Where C is the required capacitance and V is the voltage. This is then given in the last column of Table 1. Therefore, for delivery of test pulses for insulation tests of the present disclosure, a 4.7 nF (nanofarad) capacitor will guarantee a tolerable level of charge. A 33.7 nF capacitor would be considered the largest that should be used. Test capacitor 660 should therefore have a capacitance of no more than 33.7 nF.

The appropriate minimum capacitance of test capacitor 660 can be determined by the need to ensure sufficient capacitance to deliver an arc that has a duration long enough to trip overcurrent circuit 330 in case of an insulation-failure current spike. A good arc is likely if the current waveform of the circuit has a time constant T (the product of resistance and capacitance) that is greater than about 0.5 µs.

Assuming a resistance R between RV coil 40 and CAN 14 is typically about 50Ω and:

$$RC > 0.5 \text{ µs} \quad (7)$$

then:

$$C > 10 \text{ nF} \quad (8)$$

Therefore, to ensure an adequate short circuit duration the capacitance of test capacitor 660 is ideally >10 nF.

Test capacitor 660 should therefore have capacitance between about 10 nF and about 33.7 nF. A test capacitor of this size will not interfere with the therapeutic function of defibrillation. For example, assuming test capacitor 660 is a 33.7 nF capacitor, in an ICD with a 900 V maximum charge, the energy stored in the test capacitor 660 would be only 14 mJ which is negligible compared to the 40 J therapeutic shock energy.

Figure 8:
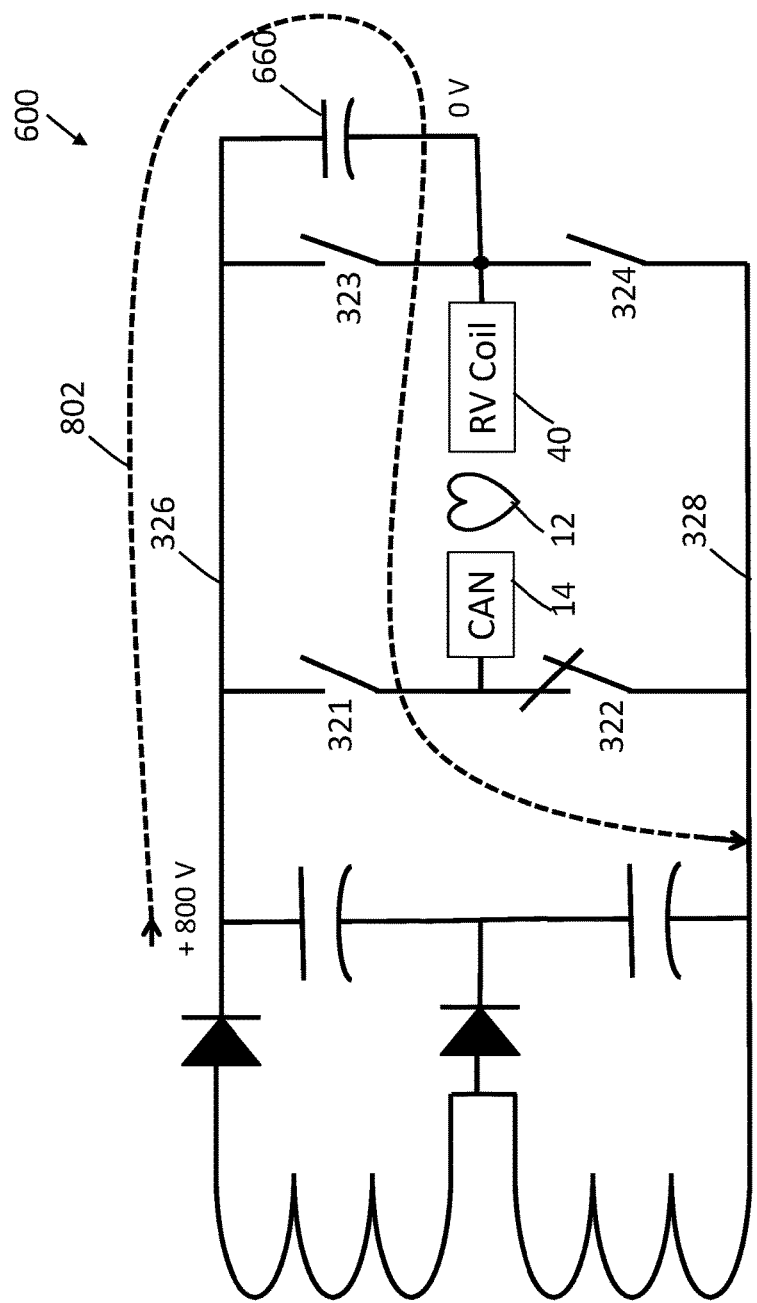
FIG. 8 is a diagram depicting the current pathway through the circuit of FIG. 6 during the delivery of a positive test pulse, according to an embodiment.

FIG. 8 depicts the current pathway 802 during the delivery of a positive test pulse over circuit 600. Therapeutic capacitors 310 and 312 are charged to the maximum voltage which is shown as a total of 800 V in this example. After therapeutic capacitors 310 and 312 are fully charged, or charged to the desired level for the insulation test, switch 323 can be closed for a few microseconds to short out (and discharge any parasitic charge) in the test capacitor, without delivery of energy to the patient. Switch 322 then is closed to allow current to flow through RV coil 40 and across chest and heart 12 to can 14. In embodiments, switch 322 can be an silicon controlled rectifier (SCR) that it will automatically open after the test capacitor is fully discharged and is no longer passing current. In other embodiments, switch 322 can be opened by ICD controller after a duration of about 0.3 to 2 microseconds. During this phase of the insulation test, the full 800 V stored in the therapeutic capacitors 310 and 312 is delivered to RV coil 40. If insulation 24 is marginal and a short circuit 42 exists between RV conductor 22 and can 14, the reduced impedance will increase the magnitude of current 802 received at can 14, and overcurrent will be sensed by overcurrent circuit 330. A cool down period of a few microseconds can elapse before delivery of the negative test pulse.

Figure 9:
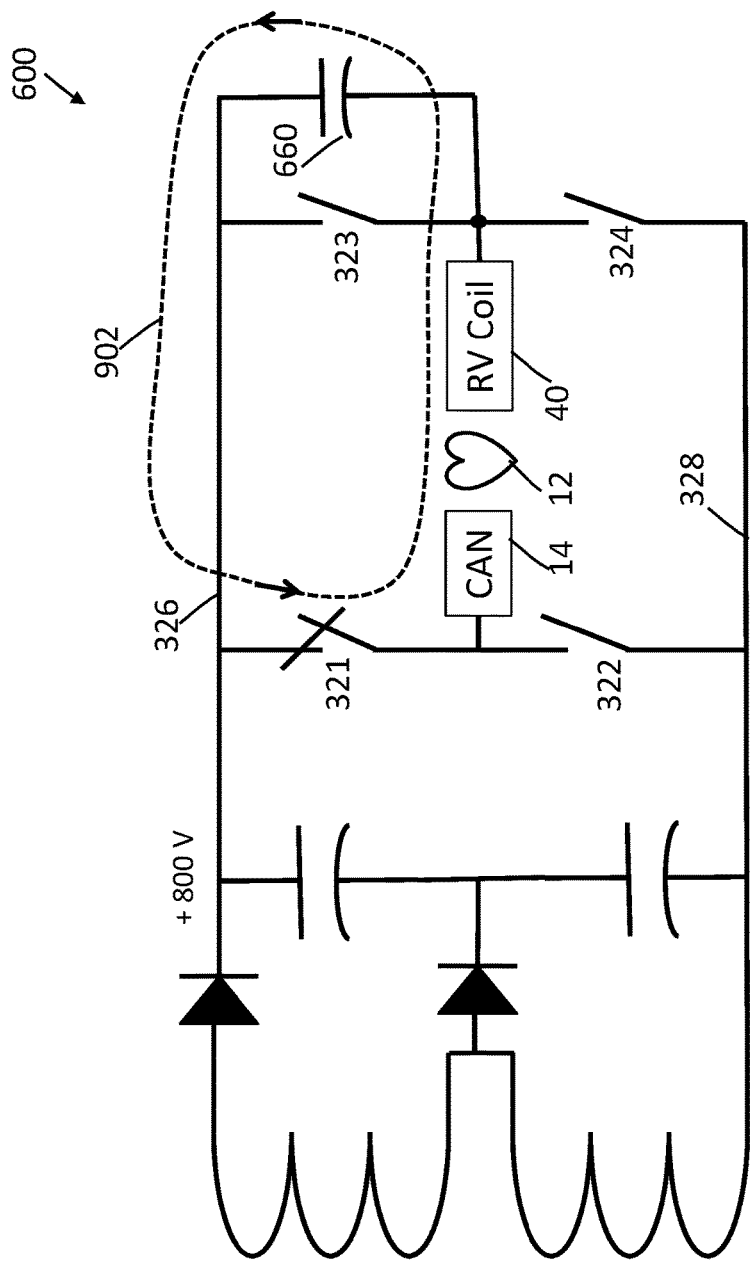
FIG. 9 is a diagram depicting the current pathway through the circuit of FIG. 6 during the delivery of a negative test pulse, according to an embodiment.
Figure 10:
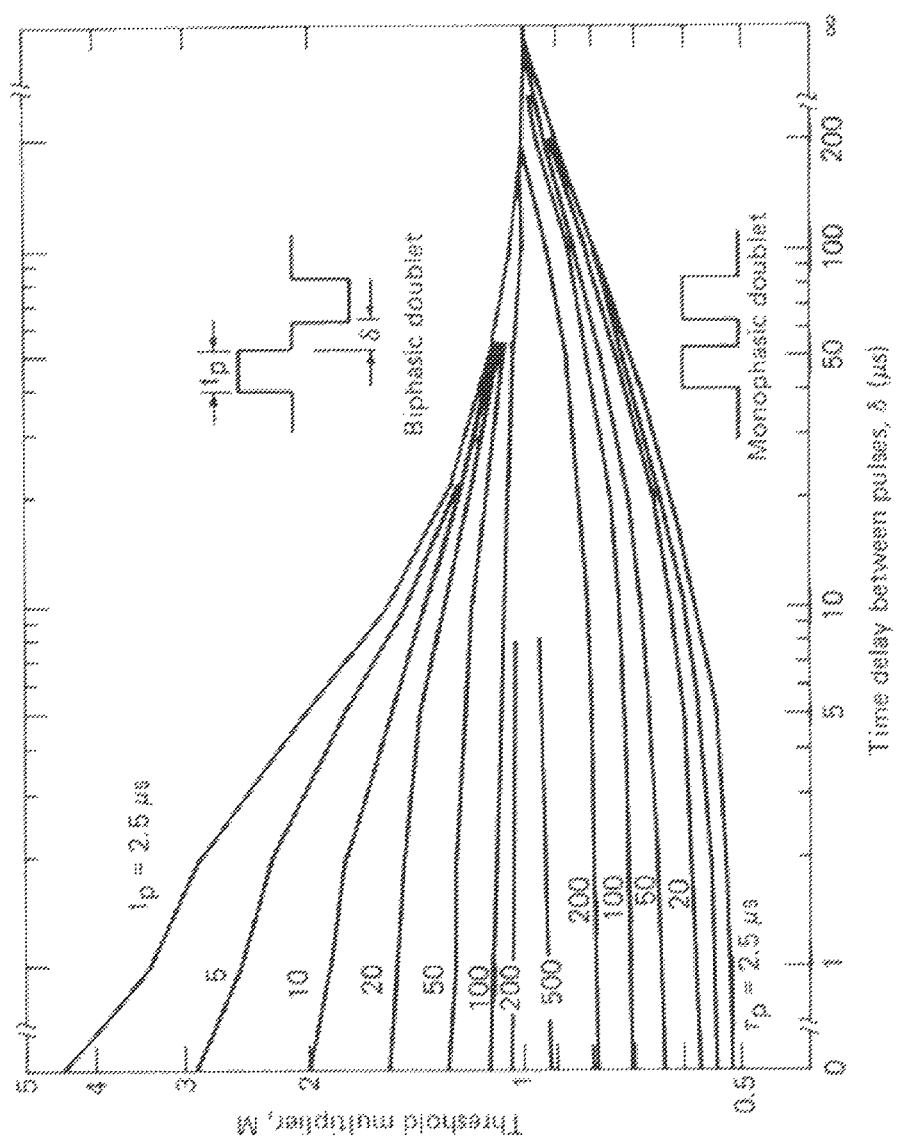
FIG. 10 is a chart depicting threshold modifiers for biphasic pulses.

FIG. 9 depicts the current pathway 902 during the delivery of a negative test pulse over circuit 600. During the cool down period, test capacitor 660 has a voltage of 800 V across it. Because a first connection of test capacitor 660, coupled to upper rail 326 and therapeutic capacitors 310 and 312, is at 800 V, the second connection of test capacitor 660 (coupled to RV coil 40) is essentially at 0 V with regards to the lower rail 328 of H-bridge 320. Closing switch 321 brings can 14 to the 800 V potential of therapeutic capacitors 310 and 312 and causes an 800 V potential difference between can 14 and RV coil 40. This delivers a short current 902 through the chest and heart of the opposite polarity of current pathway 802. This will lead to a cancellation effect for sensation by discharging most of the charge that is seen by the pain receptors. FIG. 10 is a chart depicting threshold modifiers (the inverse of the cancellation effect) for biphasic pulses.

Figure 11:
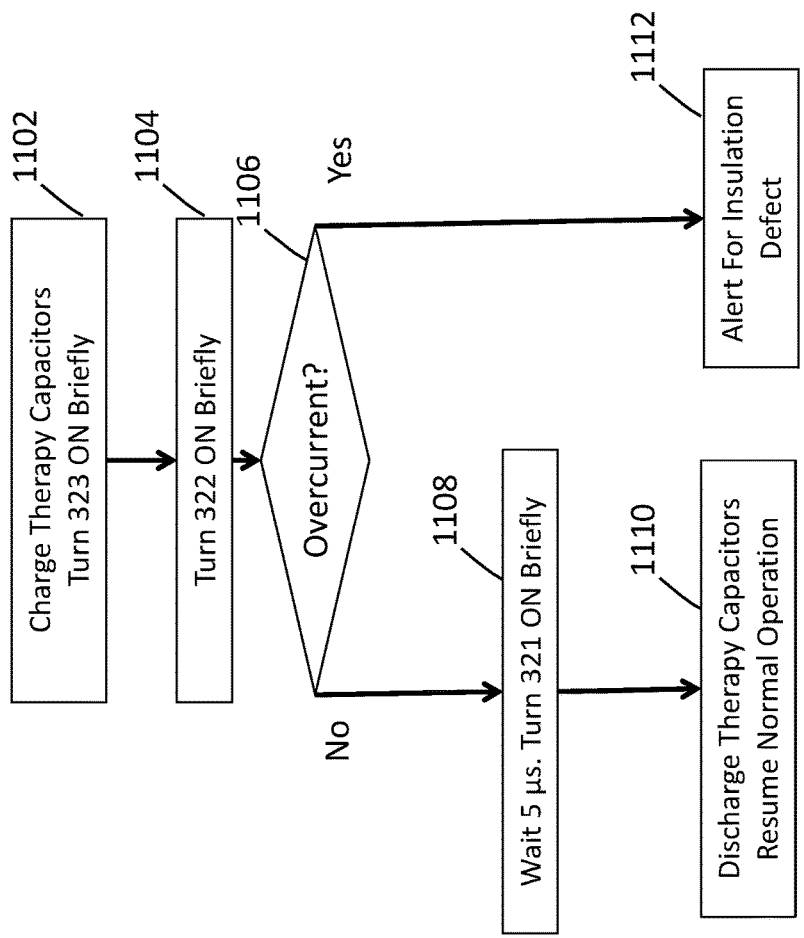
FIG. 11 is a flowchart depicting a method of lead integrity testing, according to an embodiment.

FIG. 11 is a flowchart depicting a method 1100 for lead insulation testing over circuit 600, according to an embodiment. Method 1100 can be performed during a normally scheduled capacitor reformation, or at other times. At 1102 therapeutic capacitors 310 and 312 are charged and switch 323 is closed briefly to discharge parasitic voltage in test capacitor 660 via RV coil 40. At 1104, switch 322 is closed briefly. If insulation 24 is marginal, the reduced impedance will increase the magnitude of current 802 as it passes through RV coil 40 to can 14, causing overcurrent to be sensed by overcurrent circuit 330 at 1106, and an alert signal will be sent at 1112. If no overcurrent is sensed, after a cool down period of about 5 µs, switch 321 is briefly closed at 908 to reverse the polarity of current flow over heart 12, further diminishing pain sensation.

Figure 12:
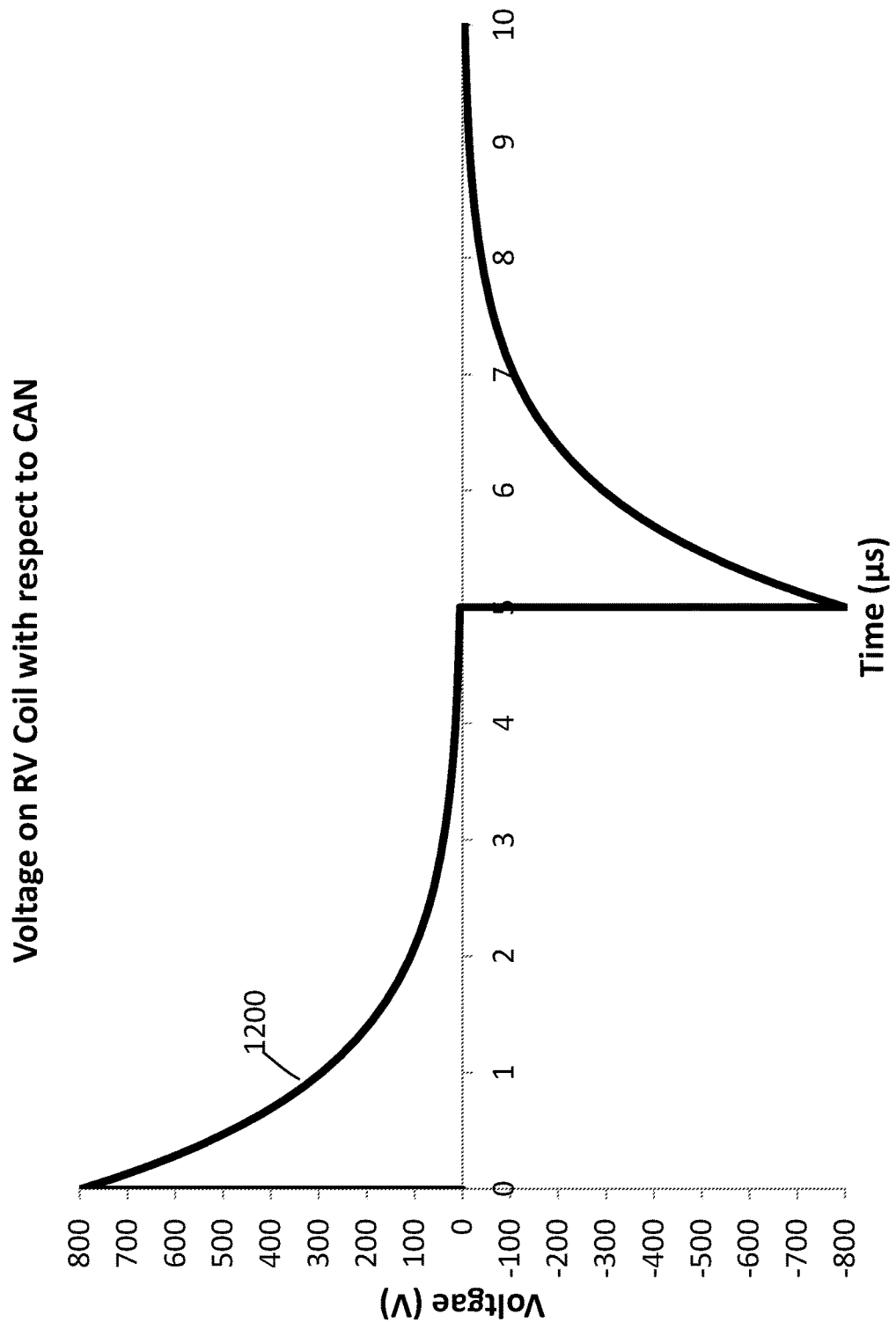
FIG. 12 is a chart depicting a voltage waveforms during a lead integrity test, according to an embodiment.

FIG. 12 is a graph depicting an example voltage waveform 1000 over circuit 600. Waveform 1200 assumes that test capacitor 660 has a capacitance of 20 nF, the resistance between RV coil 40 and CAN is 50Ω, and an 800 V charge on therapeutic capacitors 310 and 312.

Figure 13:
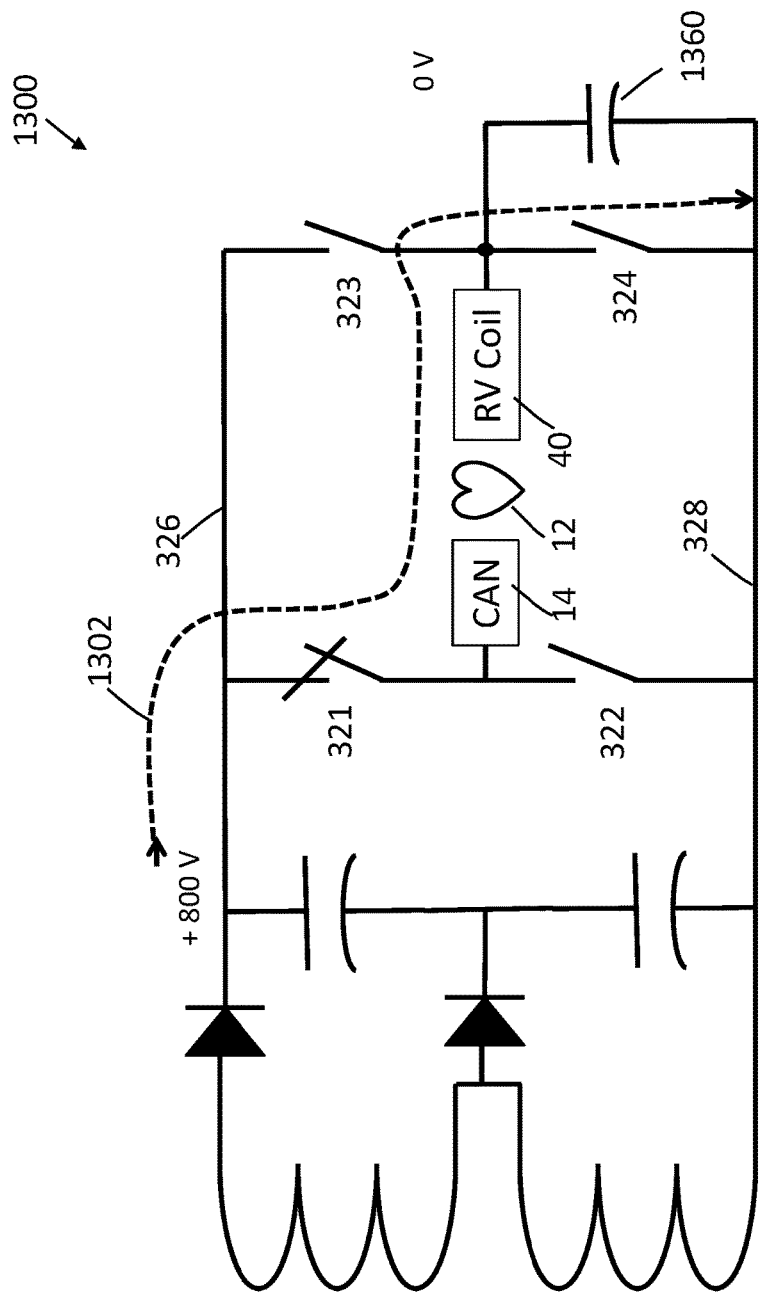
FIG. 13 is a diagram depicting the current pathway through an alternative circuit during the delivery of a positive test pulse, according to an embodiment.

FIG. 13 is a diagram depicting a modified output ICD output circuit 1300 configured to deliver test pulses for lead integrity testing according to an alternative embodiment. Circuit 1300 can be essentially equivalent to circuit 600, except that test capacitor 1360 is located across switch 324, and no test capacitor is located across switch 323. The negative-phase current flow is indicated by arrow 1302.

As with circuit 600, therapeutic capacitors 310 and 312 of circuit 1300 are charged to the maximum voltage which (800 V in this example). After therapeutic capacitors 310 and 312 are fully charged, or charged to the desired level for the insulation test, switch 324 is turned on for a few microseconds to discharge any parasitic charge in the test capacitor 1360. Then switch 321 is closed for about 0.3-2.0 µs. If switch 321 is an SCR then it will automatically turn itself off after the test capacitor is fully discharged as it is then no longer passing current. During this phase of the insulation test, the full 800 V of the therapy capacitors is delivered to can 14. This delivers a negative potential to the RV coil 40 with respect to the CAN 14 since the RV coil potential is temporarily at 0 V with respect to the lower rail 328 of the H bridge 320. If marginal insulation in lead 10 creates a short 42 between RV conductor 22 and can 14 then an overcurrent will be sensed by the overcurrent circuit 330 and an insulation defect will be detected.

Figure 14:
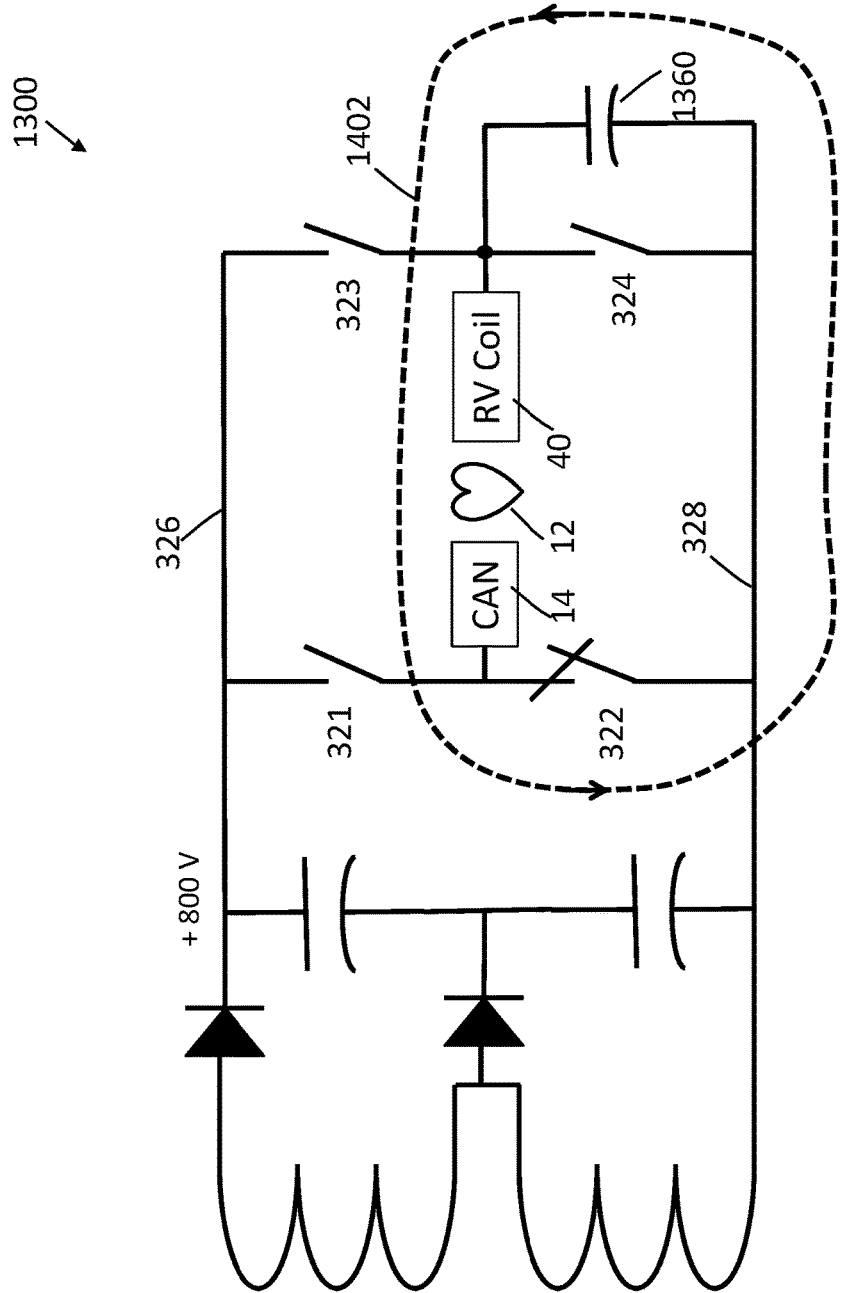
FIG. 14 is a diagram depicting the current pathway through an alternative circuit during the delivery of a negative test pulse, according to an embodiment.

FIG. 14 depicts the current pathway (arrow 1402) during the delivery of the positive test pulse across circuit 1300. During a cool down period of about 5 µs, the test capacitor has a voltage of 800 V across it. When switch 322 is closed can 14 is brought down to the 0 V of lower rail 328 of H Bridge 320. This causes an 800 V difference between the can 14 and the RV coil 40. This delivers a brief current through the chest and heart of the opposite polarity of that seen in FIG. 13. As described with respect to FIGS. 8-10, this will lead to a cancellation effect for sensation by discharging most of the charge that is seen by the pain receptors.

Figure 15:
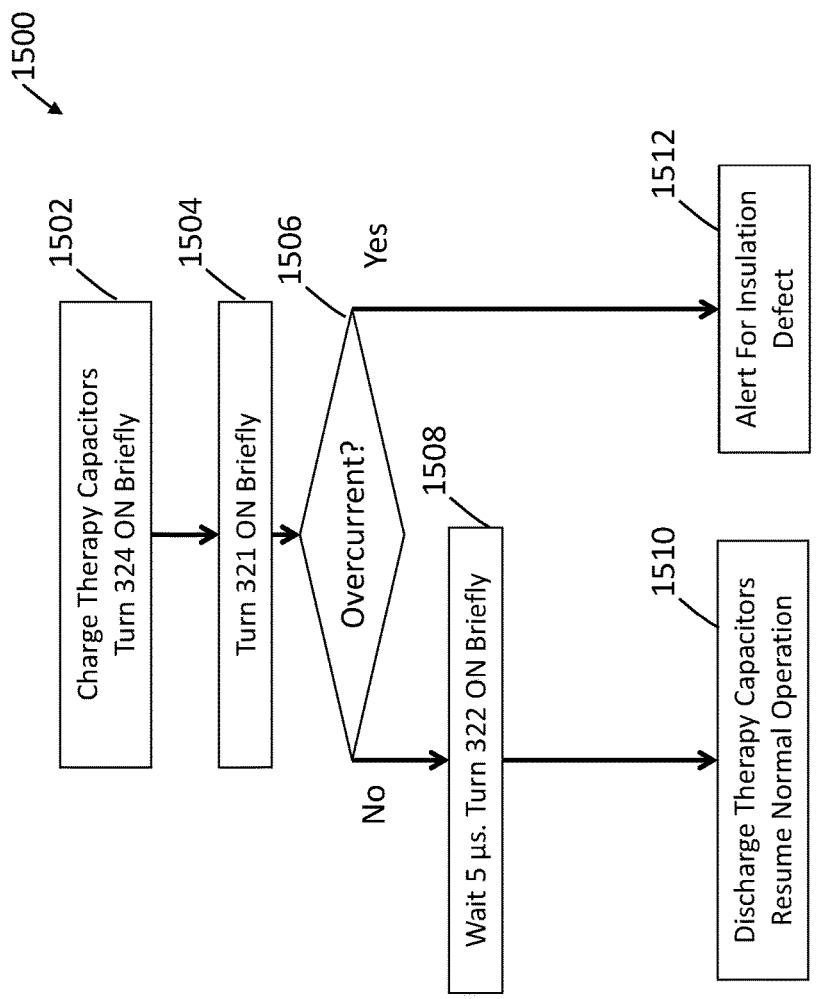
FIG. 15 is a flowchart depicting an alternative method of lead integrity testing, according to an embodiment.

FIG. 15 is a flowchart depicting a method 1500 for lead insulation testing over circuit 1300, according to an embodiment. Method 1500 is similar to method 1100. At 1502 after therapeutic capacitors 310 and 312, switch 323 is closed briefly to discharge parasitic voltage in test capacitor 1360. At 1504, switch 322 is closed briefly. If insulation 24 is marginal, the reduced impedance will increase the magnitude of current 1302 as it passes through RV coil 40 to can 14, causing overcurrent to be sensed by overcurrent circuit 330 at 1506 and an alert signal to be sent at 1512. If no overcurrent is sensed, after a cool down period of about 5 µs, switch 321 is briefly closed at 1508 to reverse the polarity of current flow over heart 12, further diminishing pain sensation.

In another embodiment of the present disclosure, the biphasic test sequence can be performed without the use of test capacitor 660 or 1160. Returning to FIG. 3, in embodiments, the H-bridge circuitry of circuit 300 can be designed such that the H-bridge can be turned cycled between off, positive, and negative rapidly enough to deliver pulses that are less than 1 µs in duration. In embodiments including test capacitor 660 or 1160, only a single leg of the H-bridge is required for testing.

As described with respect to FIG. 4, switches 322 and 323 can be closed to generate the positive phase of a biphasic pulse. Similarly, as described with respect to FIG. 5, switches 321 and 324 can be closed to generate the negative phase. While therapeutic pulses of multiple milliseconds delivered by circuit 300 can cause intolerable pain, sliver pulses with phase durations of less than 300 ns can limit pain sensation, because the total charge and duration are both very small. Therefore in embodiments, the components of H-bridge 320, specifically switches 321, 322, 323, and 324 are capable of cycling from open to closed in intervals of no more than about 300 ns, similarly the ICD controller is capable of controlling the switches at least about 3.3 MHz.

In embodiments, therapeutic capacitors 310 and 312 can be fully charged and then very short (~300 ns) sliver pulses can be delivered in order to test the insulation. As described above with respect to circuits 600 and 1000, marginal insulation will result in increased current at overcurrent sensor 330 which can be used to detect insulation degradation.

Figure 16:
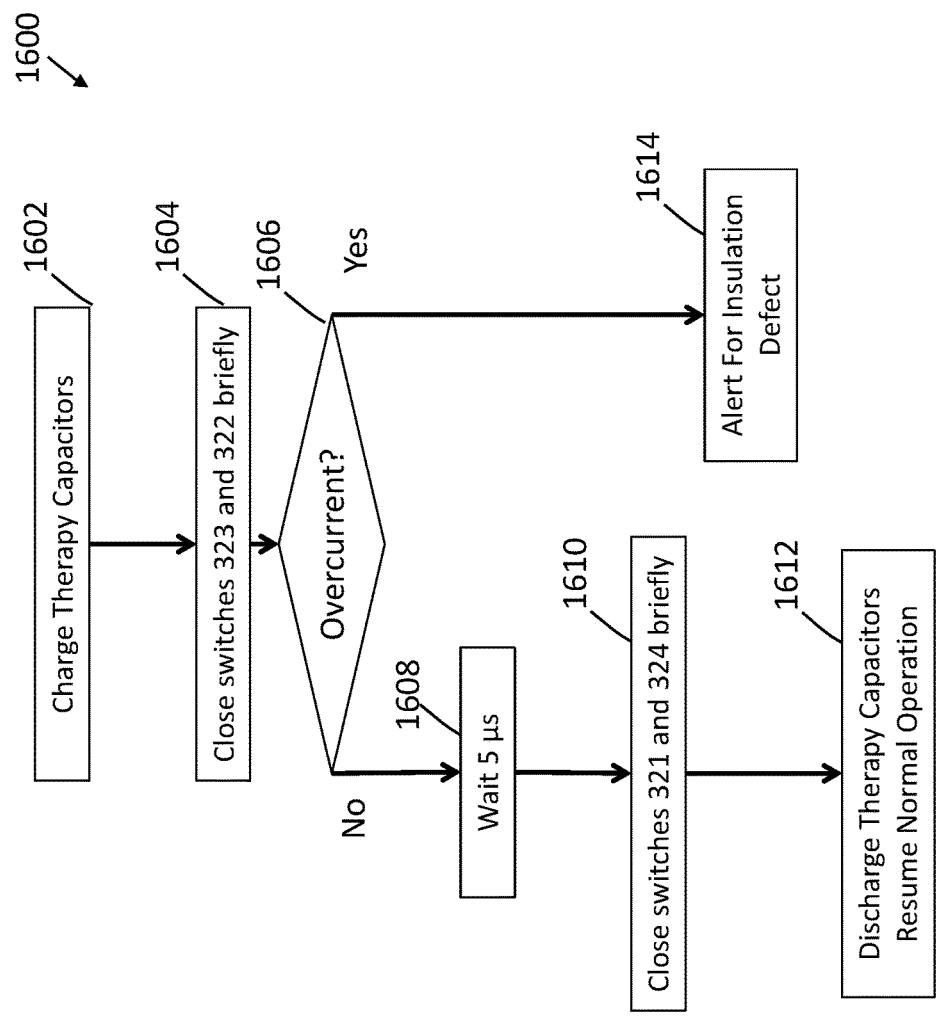
FIG. 16 is a flowchart depicting an alternative method of lead integrity testing, according to an embodiment.

FIG. 16 is a flowchart depicting a method 1600 for insulation testing over circuit 300, using high speed switches. Such switches turn OFF rapidly enough that the delivered charge is still imperceptible to the patient.

In embodiments, sliver pulses can be delivered a single time at maximum voltage or in steps, while the capacitor is charging, for example at 400, 500, 600, and 700 V. This stepped approach has the advantage of allowing a later lower-voltage temporary bailout shock. For example, if the insulation was able to withstand a 600 V shock but not an 800 V shock then the ICD would remember to use only a 600 V shock for therapy if required before the desired lead replacement. This approach is also applicable with the test capacitor embodiments. However, a larger number of sliver pulses (even delivered at lower voltages) may degrade the insulation structure and increase the chances of a short during the next therapy shock.

Sliver pulses, generated by high speed switches 321, 322, 323, 324, can be used in various clinical configurations in order to test for multiple insulation breach types, while minimizing the risk of patient pain sensation.

Figure 17:
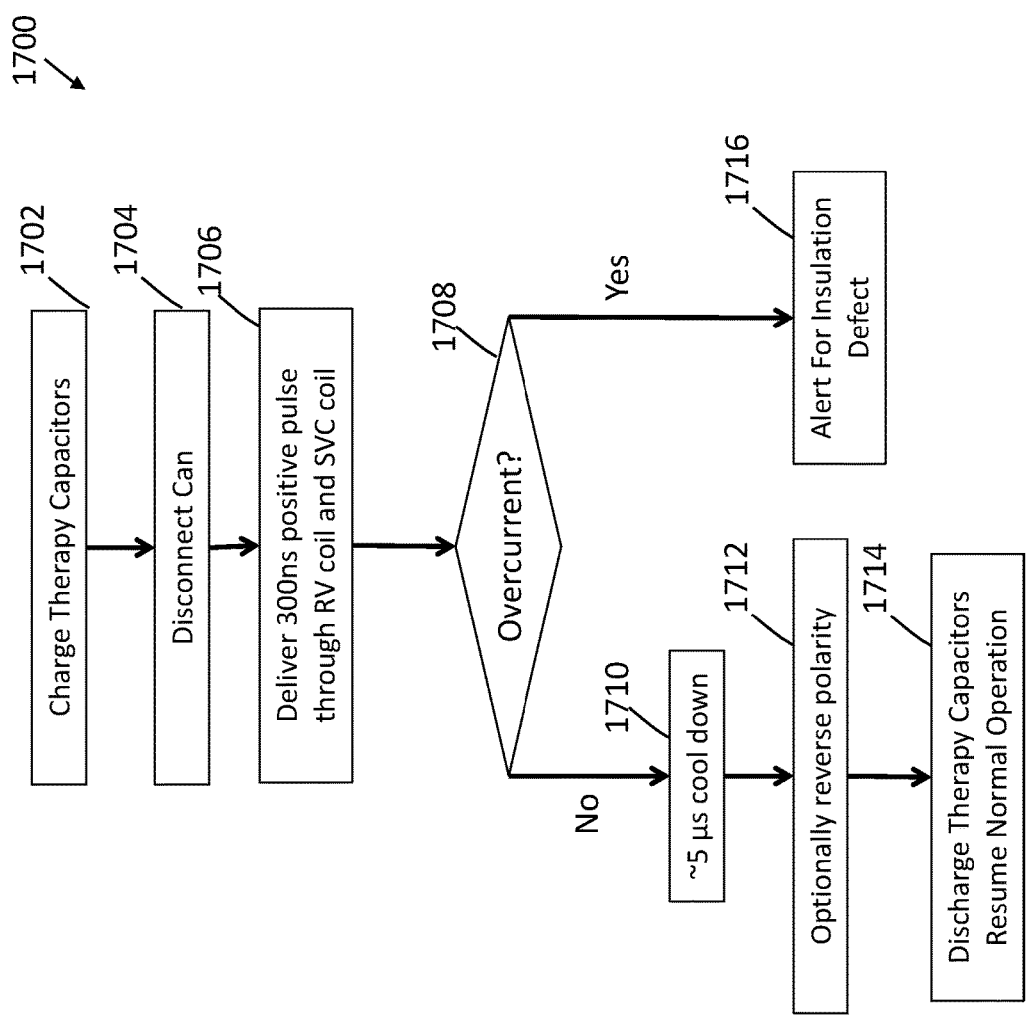
FIG. 17 is a flowchart depicting a method for detection of insulation defects in dual-coil lead a causing short between RV conductor and SVC coil, according to an embodiment.

FIG. 17 is a flowchart depicting a method 1700 for detection of insulation defects in dual-coil lead 10 a causing short between RV conductor 22 and SVC coil 38. As described above, defects under the SVC coil 38 are not apparent on fluoroscopy. Detecting this problem is straight forward using the disclosed high-speed circuit 300, and likely to be imperceptible to the patient. At step 1702, therapeutic capacitors 310 and 312 are charged. At step 1704, switches 321 and 322 are opened in order to disconnect CAN 14 from the output circuit. At 1706, switches 323 and 326 are closed for about 300 ns, delivering a positive pulse through RV coil 40 and SVC coil 38. If a short between RV conductor 22 and SVC coil 38 is detected by overcurrent 330 at 1708, an alert will be sent at 1716. Otherwise, after a cooldown of about 5 µs at 1710, switches 325 and 324 can optionally be closed at 1712 for about 300 ns in order to reverse polarity before resuming normal operation at 1714.

Because no current passes through can 14, the sensitive A-delta subcutaneous nociceptors are not stimulated by can 14. Therefore, method 1700 can allow for a large safety margin between a sufficient charge for insulation testing and the minimum charge for sensation. Polarity reversal at 1710 is therefore optional.

Figure 18:
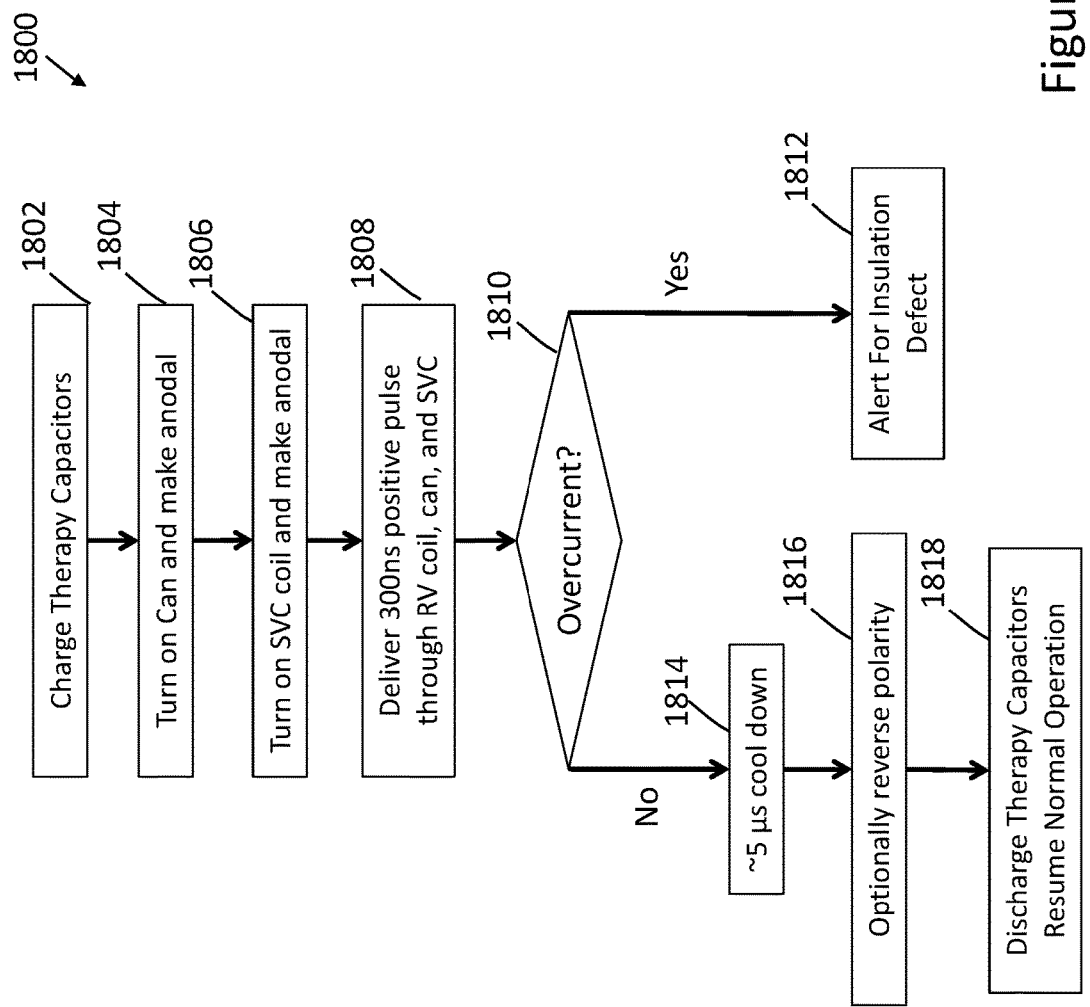
FIG. 18 is a flowchart depicting a method for detection of insulation defects in dual-coil lead causing short circuit between RV conductor and can, according to an embodiment; and, FIG. 19 is a flowchart depicting a method 1900 for detection of insulation defects causing short between RV conductor and CAN with single-coil lead, according to an embodiment.

FIG. 18 is a flowchart depicting a method 1800 for detection of insulation defects in dual-coil lead 10 causing short circuit between RV conductor 22 and can 14. In this configuration, test pulses will necessarily involve can 14 and hence patient sensation must be considered. At step 1802, therapeutic capacitors 310 and 312 are charged. At step 1804, switch 321 is closed in order to turn can 14 on and make it anodal. While this is opposite to what is desired for efficient defibrillation, this configuration will reduce the stimulation of nerve potentials proximate can 14, which are more sensitive to cathodal stimulation as can be seen in FIG. 7.

At step 1806, switch 325 is closed in order to turn SVC coil 38 on and make it anodal, in parallel arrangement with can 14. This will lower the current and charge to the can by about 50%. This charge sharing can therefore increase the safety margin for patient sensation.

At 1808, switches 321 and 324 are closed for about 300 ns, delivering a positive pulse through RV coil 40 to parallel coupling of can 14 and SVC coil 38. If a short between RV conductor 22 and can 14 is detected by overcurrent 330 at 1810, an alert will be sent at 1812. Otherwise, after a cooldown of about 5 µs at 1814, switches 323 and 322 can optionally be closed at 1816 for about 300 ns in order to reverse polarity before resuming normal operations at 1818.

Those of ordinary skill in the art will appreciate that this charge sharing can allow an 800 V, 300 ns test pulse to be delivered without patient sensation. With 800 V and assumed patient body resistance, 40Ω we expect a current of about 20 A. Thus, a 300 ns pulse will carry a total charge of 6 μC. Because the charge is shared between the can 14 and SVC coil 38 in parallel, less than half (about 3 μC) will be conducted through the CAN pocket. This is less than the previously determined tolerable charge strength of about 4.25 μC (see discussion above regarding Table 1). Therefore, as in method 1700, a cancellation phase at 1810 may be unnecessary.

Figure 19:
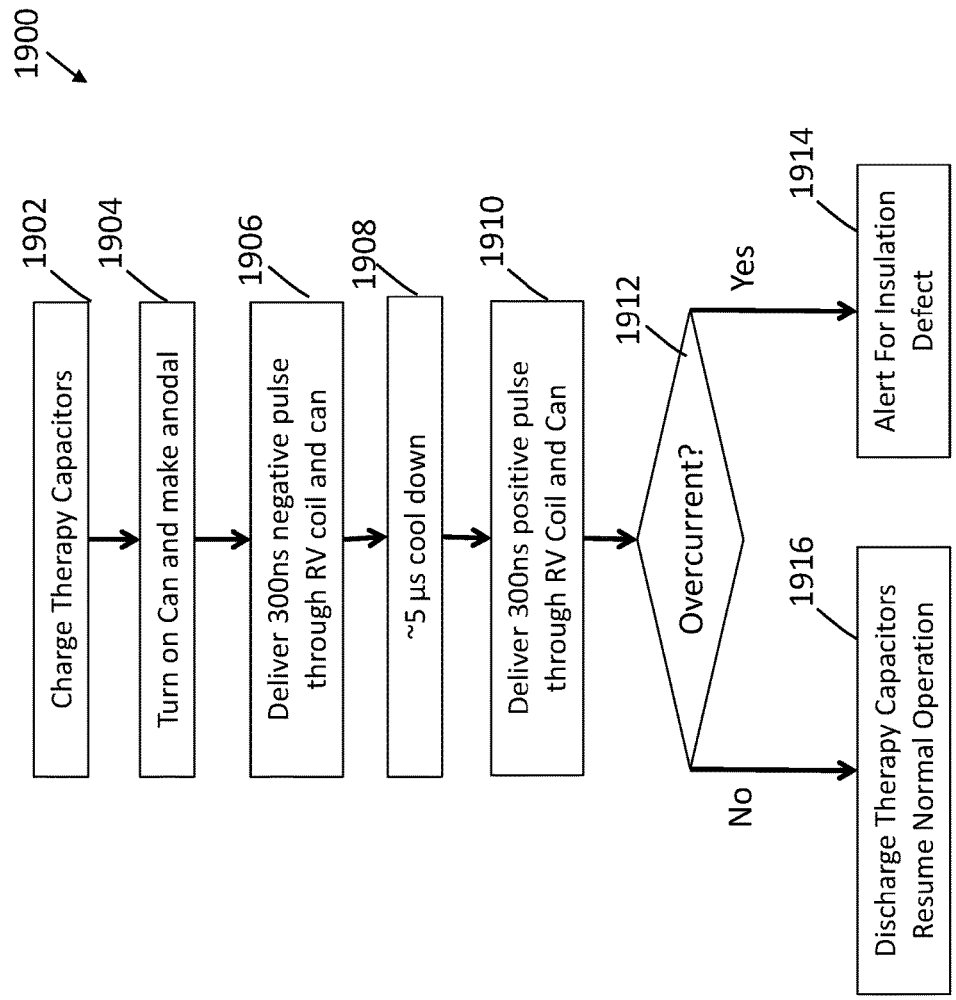

FIG. 19 is a flowchart depicting a method 1900 for detection of insulation defects causing short between RV conductor 22 and CAN 14 with single-coil lead. Because can 14 must be involved and there is no charge sharing with the SVC the test pulses are biphasic in order to reduce patient sensation during the cancellation phases.

At step 1902, therapeutic capacitors 310 and 312 are charged. At step 1904, switch 321 is closed in order to turn can 14 on and make it anodal. At step 1906, switch 324 is closed for about 300 ns to deliver a negative sliver pulse delivered from can 14 to RV coil 40. At 1914, after cool down period of about 5 μs at 1908, switch 321 is opened and switches 323 and 322 are closed for about 300 ns to deliver a positive sliver pulse from RV coil 40 to can 14. This positive sliver pulse will largely cancel the stimulation of the nerve potentials proximate can 14. Overcurrent can be detected at 1912, as shown, or after 1906, and alerted at 1914. If no overcurrent is detected, normal operation can resume at 1916.

Those of ordinary skill in the art will appreciate that a 800 V pulse through the typical single-coil impedance of 60Ω will produce a current of about 13.3 A and a total charge of about 4 μC over 300 ns. Turning again to the threshold multiplier chart of FIG. 10, it can be seen that biphasic pulses with a total duration of 6 μs (2.5 μs per phase+1 μs delay) have a cancellation factor of about 3.5 (in a conservative model assuming a 100 μs chronaxie duration). Therefore, in the present example, the effective sensation charge is about 1.1 μC which is well below any patient sensation level (see Table 1 above).

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. An implantable cardioverter defibrillator electrically connected to at least two defibrillation electrodes, at least one of the at least two defibrillation electrodes being located remotely from the defibrillator along a lead, the defibrillator comprising:
    at least one high voltage transformer electrically connected between a battery and at least one high voltage capacitor, having a positive terminal and a negative terminal;
    an H-bridge having an upper rail electrically connected to the positive terminal of the at least one high voltage capacitor, and a lower rail electrically connected to the negative terminal of the at least one high voltage capacitor, and at least two each legs,
        each leg of the at least two legs being electrically connected to a separate one of the at least two defibrillation electrodes, and
        each leg of the at least two legs further having an upper switch, electrically connected between the upper rail and the defibrillation electrode, and a lower switch, electrically connected between the defibrillation electrode and the lower rail;
    a test capacitor connected in parallel with one of the upper switch or the lower switch of a leg of the H-bridge that is connected to a defibrillation electrode on the lead;
    an overcurrent circuit, electrically connected in series between the lower rail of the H-bridge and the negative terminal of the at least one high voltage capacitor, the overcurrent circuit configured to detect current above a threshold;
    a controller, operably connected to the at least one transformer, the upper switches and lower switches of the at least two legs of the H-bridge, and the overcurrent circuit, the controller configured to:
        charge the at least one high voltage capacitor and the test capacitor,
        deliver a short duration, high-voltage, biphasic test pulse between at least two of the defibrillation electrodes, and
        produce a signal indicative of an anomaly in the lead when the overcurrent circuit detects a current above the threshold.

2. The implantable cardioverter defibrillator of claim 1, wherein the threshold is between 20 A and 40 A.

3. The implantable cardioverter defibrillator of claim 1, wherein the duration and voltage of the biphasic test pulse are chosen in order to minimize patient sensation.

4. The implantable cardioverter defibrillator of claim 1, wherein the defibrillation electrodes are chosen from the group consisting of: a can electrode, a superior vena cava coil electrode, and a right ventricular coil electrode.

5. The implantable cardioverter defibrillator of claim 1, wherein the controller delivers a short duration, high-voltage, biphasic test pulse between at least two of the defibrillation electrodes by:
   delivering a positive phase by closing the lower switch on a first leg and the upper on a second leg; and
   delivering a negative phase by opening the lower switch on the leg and the upper switch on the second leg, and closing the upper switch on the first leg and the lower switch on the second leg.

6. The implantable cardioverter defibrillator of claim 1, wherein the duration of the biphasic test pulse is one microsecond or less.

7. The implantable cardioverter defibrillator of claim 1, wherein the test capacitor has a capacitance between about 10 nF and 33.7 nF.

8. The implantable cardioverter defibrillator of claim 1, wherein the controller delivers a short duration, high-voltage, biphasic test pulse between at least two of the defibrillation electrodes by:
   delivering a positive phase by closing a first switch of a leg not including the test capacitor for a first duration;
   waiting for a cool down interval of a second duration; and,
delivering a negative phase by closing a second switch of the leg not including the test capacitor.

9. The implantable cardioverter defibrillator of claim 8, wherein the first and second switches of leg not including the test capacitor are silicon controlled rectifiers configured to open when current flow ceases.

10. The implantable cardioverter defibrillator of claim 8, wherein the first duration is between about 0.3 and 2 microseconds.

11. The implantable cardioverter defibrillator of claim 8, wherein the second duration is about 5 microseconds.

12. The implantable cardioverter defibrillator of claim 1, wherein each phase of the biphasic test pulse has a duration of less than about 300 nanoseconds.

13. The implantable cardioverter defibrillator of claim 1, wherein the voltage of the biphasic test pulse is between about 400V and about 700V.

14. The implantable cardioverter defibrillator of claim 1, wherein the controller is configured to deliver a plurality of test pulses at one or more increasing voltages.

15. A method for detecting an anomaly in a lead, the lead having at least one defibrillation electrode and operably coupled to an implantable cardioverter defibrillator, the implantable cardioverter defibrillator having a further defibrillation electrode, a test capacitor connected in parallel with one of an upper switch or a lower switch of a leg of an H-bridge connected to the defibrillation electrode, and an overcurrent circuit configured to detect current received through at least one of the defibrillation electrodes that is above a threshold, the method comprising:
   delivering a short duration, high-voltage, biphasic test pulse between two of the defibrillation electrodes by:
      delivering a positive phase test pulse of a first duration,
         waiting for a cool down interval of a second duration, and
      delivering a negative phase of a third duration; and
   detecting an anomaly in the lead when the overcurrent circuit detects a current above the threshold.

16. The method of claim 15 wherein the first duration is about 300 ns.

17. The method of claim 16 wherein the second duration is about 5 ns.

18. The method of claim 17 wherein the third duration is about 300 ns.

19. A method for detecting an anomaly in a lead, the lead, having an right ventricular coil electrode and a superior vena cava coil electrode and operably coupled to an implantable cardioverter defibrillator, the implantable cardioverter defibrillator having a can electrode, a test capacitor connected in parallel with one of the upper switch or the lower switch of a leg of an H-bridge connected to the right ventricular coil electrode or the superior vena cava coil electrode, and an overcurrent circuit configured to detect current received through at least one of the defibrillation electrodes that is above a threshold, the right ventricular coil electrode, the superior vena cava coil electrode and the can electrode being electrically connected in parallel, the method comprising:
   delivering short duration, high-voltage, positive test pulse between the right ventricular coil electrode and the can electrode and detecting a short between the can electrode and right ventricular coil electrode if the overcurrent circuit detects current above the threshold.

20. The method of claim 19, wherein the duration and voltage are chosen in order to deliver a total charge below about 4.25 µC.

21. The method of claim 20, wherein the duration is less than about 300 nanoseconds and the voltage is less than about 800V.

22. An implantable cardioverter defibrillator electrically connected to at least two defibrillation electrodes, at least one of the at least two defibrillation electrodes being located remotely from the defibrillator along a lead, the defibrillator comprising:
   at least one high voltage transformer electrically connected between a battery and at least one high voltage capacitor, having a positive terminal and a negative terminal;
   at least two circuit paths, each circuit path having a negative terminal and a positive terminal, the negative terminal of each circuit path electrically connected to the positive terminal of the at least one high voltage capacitor and the positive terminal of each circuit path electrically connected to the negative terminal of the at least one high voltage capacitor, such that each circuit path is connected in parallel to the at least one high voltage capacitor,
      each circuit path further including a first switch connected in series to the negative terminal of the circuit path and to a defibrillation electrode and a second switch connected in series to the defibrillation electrode and the positive terminal of the circuit path, each defibrillation electrode isolated from the defibrillation electrodes of the one or more other circuit paths by patient tissue;
   a test capacitor connected in parallel with one of the first switch or the second switch of the circuit path the is connected to a defibrillation electrode on the lead;
   an overcurrent circuit, electrically connected in series between the positive terminals of each circuit path and the negative terminal of the at least one high voltage capacitor, the overcurrent circuit configured to detect current above a threshold; and a controller, operably connected to the at least one transformer, the first and second switches of the at least two circuit paths and the overcurrent circuit, the controller configured to:
  charge the at least one high voltage capacitor and the test capacitor,
  deliver a short duration, high-voltage, biphasic test pulse between at least two of the defibrillation electrodes, and
  produce a signal indicative of an anomaly in the lead when the overcurrent circuit detects a current above the threshold.

* * * * *